United States Patent
Shao et al.

(10) Patent No.: US 10,998,084 B2
(45) Date of Patent: May 4, 2021

(54) SEQUENCING DATA ANALYSIS METHOD, DEVICE AND COMPUTER-READABLE MEDIUM FOR MICROSATELLITE INSTABILITY

(71) Applicant: Nanjing Shihe Gene Biotechnology Co., Ltd., Nanjing (CN)

(72) Inventors: Yang Shao, Nanjing (CN); Xue Wu, Nanjing (CN); Zhili Chang, Nanjing (CN); Xiaonan Wang, Nanjing (CN); Chongguang Yan, Nanjing (CN); Shuyu Wu, Nanjing (CN); Hua Bao, Nanjing (CN); Xiaoling Tong, Nanjing (CN)

(73) Assignee: NANJING SHIHE GENE BIOTECHNOLOGY CO., LTD., Nanjing (CN)

( * ) Notice: Subject to any disclaimer, the term of this patent is extended or adjusted under 35 U.S.C. 154(b) by 0 days.

(21) Appl. No.: 16/640,738

(22) PCT Filed: Jun. 6, 2018

(86) PCT No.: PCT/CN2018/090085
§ 371 (c)(1),
(2) Date: Feb. 21, 2020

(87) PCT Pub. No.: WO2019/047577
PCT Pub. Date: Mar. 14, 2019

(65) Prior Publication Data
US 2020/0202978 A1 Jun. 25, 2020

(30) Foreign Application Priority Data
Sep. 6, 2017 (CN) .......................... 201710795439.1

(51) Int. Cl.
*G16B 30/00* (2019.01)
(52) U.S. Cl.
CPC ................... *G16B 30/00* (2019.02)

(58) Field of Classification Search
CPC ....................................................... G16B 30/00
USPC ........................................................... 702/20
See application file for complete search history.

(56) References Cited

FOREIGN PATENT DOCUMENTS

| CN | 102230004 A | 11/2011 |
|----|-------------|---------|
| CN | 104087683 A | 10/2014 |
| CN | 106755501 A | 5/2017 |
| CN | 107335966 A | 11/2017 |
| CN | 107526944 A | 12/2017 |
| WO | 2016139534 A2 | 9/2016 |

OTHER PUBLICATIONS

Stephen J. Salipante et al., Microsatellite Instability Detection by Next Generation Sequencing, Clinical Chemistry, 2014, pp. 1-8, 60:9.
Chun Gan, et al. Applicability of Next Generation Sequencing Technology in Microsatellite Instability Testing, Genes, 2015, pp. 46-59, 6.
Guangchen Liu, Some statistical computation models and its application in biomedical information processing, Shandong University, Mar. 2016.
Fang, Chen-Yan et al., Research Progress of Lynch Syndrome-Associated Endome-trial Cancer, Journal of Chines:. Oncology, 2017, pp. 528-534, vol. 23, No. 6.

*Primary Examiner* — Jerry Lin
(74) *Attorney, Agent, or Firm* — Bayramoglu Law Offices LLC

(57) ABSTRACT

A sequencing data analysis method, a device and a computer-readable medium for microsatellite instability. The present invention can use NGS sequencing results to determine whether the microsatellite instability is present. The sequencing data analysis method can significantly improve detection sensitivity without reducing specificity, and can quickly and automatically evaluate a stable or unstable status of each MSI locus with high throughput, high sensitivity, and high specificity. By combining the statuses for all MSI loci in each sample, the samples can be comprehensively evaluated as MSS, MSI-L, or MSI-H.

18 Claims, 5 Drawing Sheets

SEQUENCING DATA ANALYSIS METHOD, DEVICE AND COMPUTER-READABLE MEDIUM FOR MICROSATELLITE INSTABILITY

CROSS REFERENCES TO THE RELATED APPLICATIONS

This application is the national phase entry of International Application No. PCT/CN2018/090085, filed on Jun. 6, 2018, which is based upon and claims priority to Chinese Patent Application No. 201710795439.1, filed on Sep. 6, 2017, the entire contents of which are incorporated herein by reference.

TECHNICAL FIELD

The present invention relates to the field of gene detection, and in particular to a method for analyzing detection results of loci indicating microsatellite instability (MSI) based on next generation sequencing technology (NGS). This method is suitable for simultaneously analyzing one or more microsatellite loci indicating MSI status, thereby accurately evaluating the MSI status of a patient, and providing a theoretical basis and guidance for the diagnosis, the prognosis, and the design of clinical treatments of the tumor.

BACKGROUND

Microsatellite instability (MSI) is a molecular phenotype that is characterized by the presence of insertion or deletion mutations in repeats of microsatellite loci in the human genome, resulting in alleles that do not exist in the standard human genome. These insertions or deletions are not corrected by the DNA mismatch repair mechanism (MMR) due to a number of reasons. The MSI phenomenon was first discovered in 1993 by Aaltonen et al. in hereditary nonpolyposis colorectal cancer (HNPCC, also known as Lynch syndrome). The common mechanism for Lynch syndrome is the presence of germline inactivation or truncation mutations in genes such as MLH1, MSH2, MSH6, PMS2, or EPCAM. Subsequently, researchers found sporadic MSI phenomena in lung cancer, digestive tract cancer, endometrial cancer, and ovarian cancer. Unlike Lynch syndrome, the cause of the sporadic MSI phenomena is mostly abnormal epigenetic modification (hypermethylation) of MLH1 gene promoter sequence, which leads to the inactivation of MLH1 gene. The incidence rates of MSI phenomenon are significantly different among various cancers. About 15% of patients with colorectal cancer show MSI tumors, while those with early-onset colorectal cancer reach 30%, and the incidence rate of MSI tumors in HNPCC is even higher than 90%.

Clinical studies have shown that stage II/III colorectal cancer patients with high-frequency MSI (MSI-H) have a good prognosis but cannot benefit from adjuvant chemotherapy with fluorouracils (e.g. 5-FU); while cancer patients with low-frequency MSI (MSI-L) have similar symptoms as microsatellite stable (MSS) cancer patients, and the prognosis for both is worse than that of MSI-H patients. Therefore, MSI detection was officially listed as the primary detection item in the International Comprehensive Cancer Network Guidelines for Colorectal Cancer Screening in 2011, which stated that the following populations should receive MSI detection:

Patients under 50 years of age who are diagnosed with colorectal cancer;

Patients with synchronous or metachronous HNPCC-like tumors, regardless of age;

Patients who have one or more first-degree relatives diagnosed with HNPCC tumors, and at least one of these relatives are less than 50 years old;

Patients who have two or more first-degree or second-degree relatives diagnosed with HNPCC-like tumors, regardless of age.

Recent studies have shown that MSI detection also plays an important guiding role in tumor immunotherapy. A number of studies have shown that colorectal patients with MSI-H display better prognosis after receiving PD-1 antibody therapy compared to patients with MSI-L or MSS. This has also been verified in other cancer types. In May 2017, the US FDA granted accelerated approval of the immunotherapeutic drug Perbrolizumab (Keytruda) for solid-tumor patients with MSI-H or DNA mismatch repair defects, who have inoperable or advanced metastases and have progressed after previous treatment. This is the first FDA-approved therapy that is primary site agnostic, herein supporting that accurately defining MSI status is of great value and guiding significance for clinical diagnosis and treatment plan development.

The common MSI detection commonly uses the following three technologies:

1. DNA mismatch repair defect detection: it directly detects gene mutations in related genes responsible for MSI phenomenon, mainly the DNA mismatch repair system (MMR) genes, or detects the level of proteins expressed by these genes via immunohistochemistry.

2. PCR detection (MSI-PCR): using specific primers, the microsatellite locus is amplified by PCR or multiplex fluorescent PCR. The amplified product is subjected to gel electrophoresis or Sanger fragment size analysis to determine whether its product fragment has a change in the migration compared with the normal control, thereby determining the MSI status.

3. NGS detection: the loci indicating the MSI status are enriched by multiplex PCR or liquid phase hybridization capture. Massively parallel sequencing combined with bioinformatics analysis is used to simultaneously evaluate the insertion/deletion mutation status of multiple MSI loci. Among these three types of techniques, traditional methods for detecting DNA mismatch repair genes, such as Sanger sequencing, have high cost but low throughput, and cannot accurately identify the inactivation of gene products caused by epigenetic abnormalities. The immunohistochemical method has shortcomings such as high requirements on sample quality, complicated operation procedures, low throughput, and over-reliance on the subjective view of the pathologists. MSI detection based on PCR technology can directly assess the instability of microsatellite loci, but it is restricted by its complicated operation, long time consumption, low throughput, poor sensitivity, and low reproducibility. Although multiplex PCR detection improves testing throughput, the interaction among several sets of primers is very complex, which limits the number of microsatellite loci that can be assessed in one assay, indirectly increases the difficulty in accurately separating the high-frequency MSI-H and low-frequency MSI-L, and significantly increases the cost and difficulty in exploring additional MSI loci or removing certain MSI loci. Unlike the first two types of technologies, despite of its high total cost, NGS permits simultaneous assessment of other genetic features along with MSI evaluation. NGS technology has the advantage of high throughput, high precision, and high sensitivity, which indirectly reduces the cost for a single detection. Therefore, it is gradually accepted by more and more users. In the meanwhile, it has been realized that the NGS-based detection methods impose extremely high technical requirements on data analysis. Due to the lack of a consensus over method of analysis or a standardized guideline, effectively, accurately and objectively define the microsatellite stable/unstable status of each locus through bioinformatics algorithms has become one of the prime technical challenges.

Regarding the choice of microsatellite loci for MSI detection, the US National Cancer Institute (NCI) issued the Bethesda guideline in 1997, which recommend five microsatellite loci (BAT-26, BAT-25, D2S123, D5S346, D17S250) that can be used for MSI detection in colorectal cancer. In addition, the guideline classifies and defines the categories of MSI, namely:

1. High frequency MSI (MSI-H): Two or more of the recommended loci show changes in length of the repeat;
2. Low frequency MSI (MSI-L): One of the recommended loci shows the change in length of the repeat;
3. Microsatellite stabilization (MSS): There is no change in the length of the repeat in the recommended loci.

Among the initial five recommended loci proposed by Bethesda guideline, the stability of three loci with dinucleotide repeat units (D2S123, D5S346 and D17S250) was found controversial at the 2002 NCI meeting: the Suraweera research team pointed out that for patients with MSI-H, the detection sensitivity can be improved when the three loci above are replaced by the following three loci with mononucleotide repeat units, NR21, NR22 and NR24. In 2004, the Bacher research group showed that the test sensitivity with the mononucleotide repeat loci was 92%-100%, and the specificity for MSI-H cases was as high as 99.5%-100%. This conclusion was further confirmed by the Rosa M. Xicola group in 2007. In addition to the Bethesda guideline, Promega Biotechnology Co., Ltd. developed its own MSI analysis system, which uses the mononucleotide repeat locus, Mono27, to replace the NR22 proposed by Suraweera et al., and adds two loci with 5 bp repeating units, Penta C and Penta D that are highly diverse in the human population, for sample quality control.

Based on the detection method developed by Bethesda guidelines, since only 5 MSI loci are evaluated, the final result lacks continuity and only shows the strata of 20%, 40%, 60%, 80%, 100%, causing high risk of misclassification of MSI-H and MSI-L for samples with values close to the determination threshold. Therefore, increasing the MSI loci can improve the clarity of the test and provide a mathematical and statistical basis for accurate determination of MSI-H and MSI-L. As a result, there is an urgent need to develop a MSI-related-locus-searching method for scientifically and efficiently screening genomic loci that can indicate MSI status.

SUMMARY

The objective of the present invention is to solve the problem that the current commercial Promega MSI detection kit which can only detect 5 MSI loci (BAT-25, BAT-26, MONO-27, NR-21, NR-24), generating results with poor continuity and large gaps, causing high risk of misclassification of MSI-H and MSI-L for samples close to the determination threshold. The present invention proposes a combination comprising 22 MSI loci, which can be used for microsatellite instability determination. The gradient gaps are greatly reduced and the same detection accuracy as the Promega kit can be achieved by this invention.

In the meanwhile, the present invention can also solve the low sensitivity problem present by using conventional MSI sequencing to determine the MSI status of the microsatellite locus. The present invention provides a bioinformatics analysis method applied to MSI data detected by NGS. This determination method allows the determination of the microsatellite instability status using NGS sequencing results, and the analytical calculation method can significantly improve the detection sensitivity without reducing the specificity, and can evaluate the stable or unstable status of each MSI locus quickly and automatically with high-throughput, high-sensitivity, and high specificity. With a combination of the statuses for all MSI loci in each sample, the sample can be comprehensively evaluated as MSS, MSI-L, or MSI-H. The present invention also provides a set of screening methods for screening potential MSI loci based on this analytical method, which can be applied to the entire exome NGS, or any DNA NGS platform with customized target gene or sequence panel, to accurately screen the loci in the target panel suitable for determining the MSI status of the sample.

The First Aspect of the Invention:

A combination of loci for detecting microsatellite instability, including any 16, 17, 18, 19, 20, 21, and 22 of the following twenty-two (22) gene loci: BAT25, BAT26, NR24, NR21, Mono27, NR22, NR27, BAT40, CUL-22, MET-15, ATM-15, RB1-13, NF1-26, DDR-11, FANC-21, MITF-14, PKHD-18 PTK-16, RET-14, CBL-17, PTPN-17, and SMAD-18; the positions of the microsatellite loci in the genome are shown in Table 1.

TABLE 1

Twenty-two (22) loci for detecting microsatellite instability

| Locus number | Microsatellite locus name | Repeat unit (number) | Genomic location (Human Hg19) |
|---|---|---|---|
| MS-1 | BAT-25 | T(25) | chr4: 55,598,212-55,598,236 |
| MS-2 | BAT-26 | A(27) | chr2: 47,641,560-47,641,586 |
| MS-3 | NR-24 | T(23) | chr2: 95,849,362-95,849,384 |
| MS-4 | NR-21 | T(21) | chr14: 23,652,347-23,652,367 |
| MS-5 | Mono-27 | A(27) | chr2: 39,536,690-39,536,716 |
| MS-6 | NR-22 | T(21) | chr11: 125,490,766-125,490,786 |
| MS-7 | NR-27 | A(26) | chr11: 102,193,509-102,193,534 |
| MS-8 | BAT-40 | T(37) | chr1: 120,053,341-120,053,377 |
| MS-9 | CUL-22 | A(22) | chr2: 225,422,601-225,422,622 |
| MS-10 | MET-15 | T(15) | chr7: 116,409,676-116,409,690 |
| MS-11 | ATM-15 | T(15) | chr11: 108,114,662-108,114,676 |
| MS-12 | RB1-13 | T(13) | chr13: 48,954,160-48,954,172 |
| MS-13 | NF1-26 | T(26) | chr17: 29,559,062-29,559,087 |
| MS-14 | DDR-11 | A(1) | chr1: 162,736,822-162,736,832 |
| MS-15 | FANC-21 | A(21) | chr3: 10,076,009-10,076,029 |
| MS-16 | MITF-14 | T(14) | chr3: 69,988,438-69,988,451 |
| MS-17 | PKHD-18 | A(18) | chr6: 51,503,598-51,503,615 |
| MS-18 | PTK-16 | A(16) | chr8: 141,754,889-141,754,904 |
| MS-19 | RET-14 | T(14) | chr10: 43,595,837-43,595,850 |
| MS-20 | CBL-17 | T(17) | chr11: 119,144,792-119,144,808 |
| MS-21 | PTPN-17 | T(17) | chr12: 112,893,676-112,893,692 |
| MS-22 | SMAD-18 | A(18) | chr18: 45,395,846-45,395,863 |

In one embodiment, the locus combination contains all 22 loci.

In one embodiment, all combinations further comprises one or more of the following genes: AKT1, CTNNB1, FLT3, KRAS, PTPN11, SRC, ALK, EGFR, GNAS, MLH1, RB1, STK11, ATM, ERBB2, HNF1A, MPL, RAD50, TP53, BRAF, ERBB4, IDH1, NRAS, RET, VHL, BRCA1, BRCA2, FBXW7, JAK3, PIK3CA, SMAD4, CDH1, FGFR2, KIT, PTEN, SMARCB1, ABL1, CSF1R, GNA11, JAK2, NOTCH1, SMO, APC, FGFR1, GNAQ, KDR, NPM1, CDKN2, FGFR3, HRAS, MET, or PDGFRA.

The Second Aspect the Invention:

A kit for detecting the locus combinations described.

The kit contains probes or primers specifically binding to the microsatellite loci listed in the locus combinations.

The Third Aspect of the Invention:

The application of the above locus combinations in the preparation of microsatellite instability detection reagents.

The microsatellite instability detecting reagent is for detecting cancer in a mammal, and the cancer includes, but is not limited to, colorectal cancer, endometrial cancer, ovarian cancer and gastro-intestinal tract cancer.

In the described application, the process of microsatellite instability detection refers to the steps described by the fourth aspect of the invention.

The Fourth Aspect of the Invention:

A method for analyzing sequencing data of microsatellite instability, comprising the following steps:

S1: performing NGS sequencing on test samples and normal samples to obtain the sequencing data spanning MSI locus to be determined in the test samples and the normal samples;

S2: for the sequencing data obtained in the step S1, using any one of the following three criteria for analysis, and if any of the criteria is satisfied, then determining that the MSI locus of the test sample is unstable;

S2-1: according to the sequencing data obtained in the step S1, calculating principal repeat unit species at the MSI locus for each of the test samples and each of the normal samples; tallying number $N_i$ of the principal repeat unit species in each of the normal samples, and calculating mean value [mean($N_i$)] of the $N_i$ and standard deviation [sd($N_i$)]; if the number of the principal repeat unit species at the locus in the test sample is larger than mean($N_i$)+x*sd($N_i$), then determining that the MSI locus in the test sample is an unstable microsatellite locus, wherein x is a coefficient of standard deviation, preferably 3;

S2-2: according to the sequencing data obtained in the step S1, calculating the principal repeat unit species at the MSI locus of each of the test samples and each of the normal samples; and if a principal repeat unit species that has not appeared in any of the normal samples is found in the test sample at the MSI locus, then determining that the MSI locus in the test sample is an unstable microsatellite locus; and S2-3: according to the sequencing data obtained in the step S1, pooling all of the normal samples as a whole, calculating a population principal repeat unit species in all of the normal samples, and then calculating a proportion of the population principal repeat unit species in each of the normal samples, performing statistical analysis according to the proportion to obtain a distribution reference set and calculate median [Q2 ($R_i$)], first quartile [Q1($R_i$)], and third quartile [Q3($R_i$)] of the proportion; and calculating a proportion ($RT_i$) of the population principal repeat unit species in each of the test samples; and if $RT_i$>Q2($R_i$)+1.5*(Q3($R_i$)−Q1($R_i$)) or $RT_i$<Q2($R_i$)−1.5*(Q3($R_i$)−Q1($R_i$)), then determining that the MSI locus in the test sample is an unstable microsatellite locus.

In one embodiment, the sequencing data analysis method is for non-therapeutic and non-diagnostic purposes.

In one embodiment, the principal repeat unit species in the steps S2-1 and S2-2 are calculated by the following method:

S3-1: according to a sequencing result of one of the samples, tallying a number of sequencing reads corresponding to repeat units with different numbers of repeating base pairs spanning the MSI locus, and total number ($n_{total}$) of the sequencing reads corresponding to all of the repeat units at the MSI locus;

S3-2: sorting the repeat units with the different numbers of the repeating base pairs in descending order according to their corresponding numbers of the sequencing reads, recording the number of the sequencing reads as n(j), wherein j=1, 2, 3 . . . etc.; individually calculating a percentage [A(j)] of the n(j) to the total number of the sequencing reads: A(j)=n(j)/$n_{total}$*100%; and S3-3: sequentially calculating a cumulative percentage B for m=1, 2, 3 . . . etc., using the formula below:

$$B = \sum_{j=1}^{m} A(j);$$

once B≥a threshold percentage, stop the calculation and define the repeat unit species corresponding to A(1) to A(m) as the principal repeat unit species; wherein the threshold percentage is preferably 90%.

In one embodiment, the population principal repeat unit species in the step S2-3 is calculated by the following steps:

S4-1: pooling the sequencing data of all of the normal samples as a whole, and tallying a number of sequencing reads corresponding to repeat units with different numbers of repeating base pairs spanning the MSI locus, and total number ($n_{total}$) of the sequencing reads corresponding to all of the repeat units at the MSI locus;

S4-2: sorting the repeat units with the different numbers of the repeating base pairs in descending order according to their corresponding numbers of the sequencing reads, recording the number of the sequencing reads as n(j), wherein j=1, 2, 3 . . . etc.; individually calculating a percentage [A(j)] of the n(j) to the total number of the sequencing reads: A(j)=n(j)/$n_{total}$*100%; and S4-3: sequentially calculating a cumulative percentage B for m=1, 2, 3 . . . etc., using the formula below:

$$B = \sum_{j=1}^{m} A(j);$$

as soon as B≥a threshold percentage, stopping the calculation and defining the repeat units with the different numbers of the repeating base pairs corresponding to A(1) to A(m) as the population principal repeat unit species, wherein the threshold percentage is preferably 90%.

In one embodiment, in the step S2-3, calculating the proportion of the population principal repeat unit species in each of the normal samples is performed by counting a number (n) of sequencing reads corresponding to each of the population principal repeat unit species at the MSI locus in each of the normal samples, and then calculating a proportion of the number (n) of the sequencing reads to a total number ($n_{total}$) of sequencing reads spanning the MSI locus in the normal sample.

In one embodiment, the analyzing method further comprises step S5: calculating a proportion of the microsatellite loci determined to be unstable among all tested microsatellite loci, and performing statistical analysis on the proportion data of the samples to qualitatively determine thresholds used to define the samples as MSS, MSI-L or MSI-H.

In one embodiment, target gene DNA is enriched by a liquid phase capture method in the NGS process in step S; more preferably, the target gene DNA is enriched by 120 bp biotinylated single-stranded DNA probes through liquid phase capture in the NGS process.

In one embodiment, three determination criteria are simultaneously used for the determination in step S2. If at least one criterion is satisfied, the microsatellite locus of the sample is considered as unstable.

In one embodiment, the described MSI loci are mononucleotide repeat units.

In one embodiment, the above described microsatellite instability sequencing data analysis method may be constructed by combining S2-1 with S5, S2-2 with S5, or S2-3 with S5, for S1 and S2.

The fifth aspect of the Invention:

A device for detecting microsatellite instability, characterized by that the device comprises of:

a sequencing data reading module configured to read sample sequencing data obtained and stored from a sequencing device;

a principal repeat unit species determining module configured to analyze the sample sequencing data to obtain principal repeat unit species of a microsatellite locus in each of normal samples or test samples;

a population principal repeat unit species determining module configured to analyze the sample sequencing data to obtain population principal repeat unit species in all of the normal samples;

a determining module configured to determine whether the MSI locus is in an unstable status, and include one or more of first, second and third analyzing modules, wherein the first analyzing module is configured to obtain the principal repeat unit species at the MSI locus of each of the test samples and normal samples obtained from the principal repeat unit species determining module, tally a number ($N_i$) of the principal repeat unit species in each of the normal samples, and calculate mean value [mean($N_i$)] of the $N_i$ and standard deviation [sd($N_i$)]; if the number of the principal repeat unit species at the locus in the test sample is larger than mean($N_i$)+x*sd($N_i$), then the MSI locus in the test sample is determined as an unstable microsatellite locus, wherein x is a coefficient of standard deviation, preferably 3 the second analyzing module is configured to obtain the principal repeat unit species at the MSI locus of each of the test samples and the normal samples obtained from the principal repeat unit species determining module, and determine whether a principal repeat unit species that has not appeared in any of the normal samples is present in the test sample at the MSI locus; if present, then the MSI locus in the test sample is determined as an unstable microsatellite locus;

the said third analyzing module is configured to obtain the population principal repeat unit species of all normal samples obtained, calculate the proportion of these repeat unit species in each normal sample, analyze the proportion set of individual normal samples to generate the distribution reference set, and determine the median [$Q2(R_i)$], the first quartile [$Q1(R_i)$] and the third quartile [$Q3(R_i)$] of the distribution reference set; the proportion of the population principal repeat unit species within each test sample ($RT_i$) is calculated, and the MSI locus in the test sample is considered as unstable if $RT_i$ satisfies the following condition:

$RT_i > Q2(R_i) + 1.5*(Q3(R_i) - Q1(R_i))$ or $RT_i < Q2(R_i) - 1.5*(Q3(R_i) - Q1(R_i))$.

In one embodiment, the determining module comprises the first, second and third analyzing modules, and the determining module is configured to obtain analysis results from the first, second and third analyzing modules, and if the analysis results from any one of the first, second and third analyzing modules show microsatellite instability status, then the determining module determines that the test sample is in a microsatellite instability status.

In one embodiment, the principal repeat unit species determining module is configured to tally a number of sequencing reads corresponding to repeat units with different numbers of repeating base pairs spanning the MSI locus, and total number ($n_{total}$) of the sequencing reads corresponding to all of the repeat units at the MSI locus, according to a sequencing result of one of the samples; sort the repeat units with the different numbers of the repeating base pairs in descending order according to their corresponding numbers of the sequencing reads, the number of the sequencing reads being recorded as n(j), wherein j=1, 2, 3 . . . etc.; individually calculate a percentage [A(j)] of the n(j) to the total number of the sequencing reads: $A(j) = n(j)/n_{total}*100\%$; and sequentially calculate a cumulative percentage B for m=1, 2, 3 . . . etc., using the formula below:

$$B = \sum_{j=1}^{m} A(j);$$

wherein when B≥a threshold percentage, the calculation is stopped and the repeat units with the different numbers of the repeating base pairs corresponding to A(1) to A(m) are determined as the principal repeat unit species; and the threshold percentage is preferably 90%.

In one embodiment, the population principal repeat unit species determining module is configured to pool the sequencing data of all of the normal samples as a whole, tally a number of sequencing reads corresponding to repeat units with different numbers of repeating base pairs spanning the MSI locus, and total number ($n_{total}$) of the sequencing reads corresponding to all of the repeat units at the MSI locus; sort the repeat units with the different numbers of the repeating base pairs in descending order according to their corresponding numbers of the sequencing reads, the number of the sequencing reads being recorded as n(j), wherein j=1, 2, 3 . . . etc.; individually calculate a percentage [A(j)] of the n(j) to the total number of the sequencing reads: $A(j) = n(j)/n_{total}*100\%$; and sequentially calculate a cumulative percentage B for m=1, 2, 3 . . . etc., using the formula below:

$$B = \sum_{j=1}^{m} A(j);$$

wherein when B≥a threshold percentage, the calculation is stopped and the repeat units with the different numbers of the repeating base pairs corresponding to A(1) to A(m) are determined as the population principal repeat unit species; and the threshold percentage is preferably 90%.

In an embodiment, a threshold calculating module is further included, configured to calculate the proportion of unstable microsatellite loci within all microsatellite loci, and statistically analyze the proportion data for defining the thresholds of MSS, MSI-L or MSI-H.

In one embodiment, the device for detecting microsatellite instability could be composed of a sequencing data reading module, a principal repeat unit species determining module and a determining module including the first analyzing module; a sequencing data reading module, a principal repeat unit species determining module and a determining module including the second analyzing module; or a sequencing data reading module, a population principal repeat unit species determining module, and a determining module including the third analyzing module.

The sixth aspect of the Invention:

A computer readable medium, which records programs for performing the microsatellite instability analysis methods described above.

In summary, the present invention develops a data analysis method based on the microsatellite instability detection of the next generation sequencing technology, and a screening method for searching a genomic locus suitable for use as a microsatellite instability indicator in the genome. The analytical method and the screening method can be selectively applied to various gene detection technologies compatible with whole exome sequencing or targeted sequencing, and provide great theoretical and clinical guide significant for the treatment strategy and prognosis of related cancers.

The MSI-related microsatellite locus detection method developed based on the present invention has advantages of high throughput, high sensitivity, high resolution, high repeatability, objectivity, and simple operation compared with the conventional MSI detection. It also has the following beneficial effects compared with other analysis approach based on the next generation sequencing technology:

On one hand, the determining method for identifying the stable status of a microsatellite locus provided by the present invention determines the microsatellite instability from three different point-of-views, and thus has a higher sensitivity. In the meanwhile, the detection method did not show a decrease in specificity accompanying with an increase in sensitivity. The high sensitivity and high specificity of this method directly advance the accuracy of distinguishing MSS, MSI-L, and MSI-H samples. On the other hand, the selection of the MSI loci of the present invention is limited to the enrichment method based on the NGS, and thus it is not necessary to specifically design an enrichment method for the microsatellite loci, which avoids the risk of introducing off-target enrichment by additional enrichment probes or PCR primers. The screening process for MSI loci combines both theoretical assumptions and the practical performance of the candidate loci in the clinical samples, to ensure the value of the selected loci in clinical application.

DETAILED DESCRIPTION OF THE EMBODIMENTS

Figure 1:
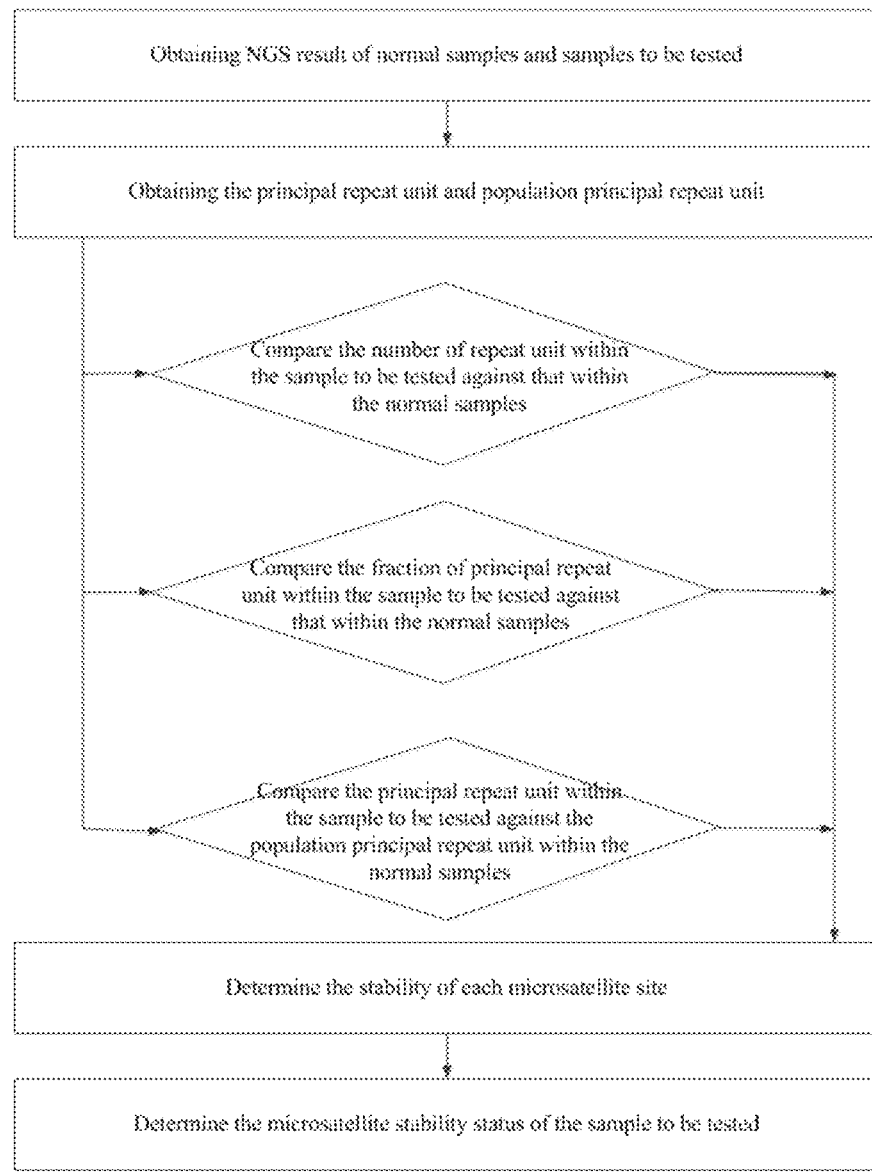
FIG. 1: Flow chart of microsatellite locus detection method provided by the present invention.
Figure 2:
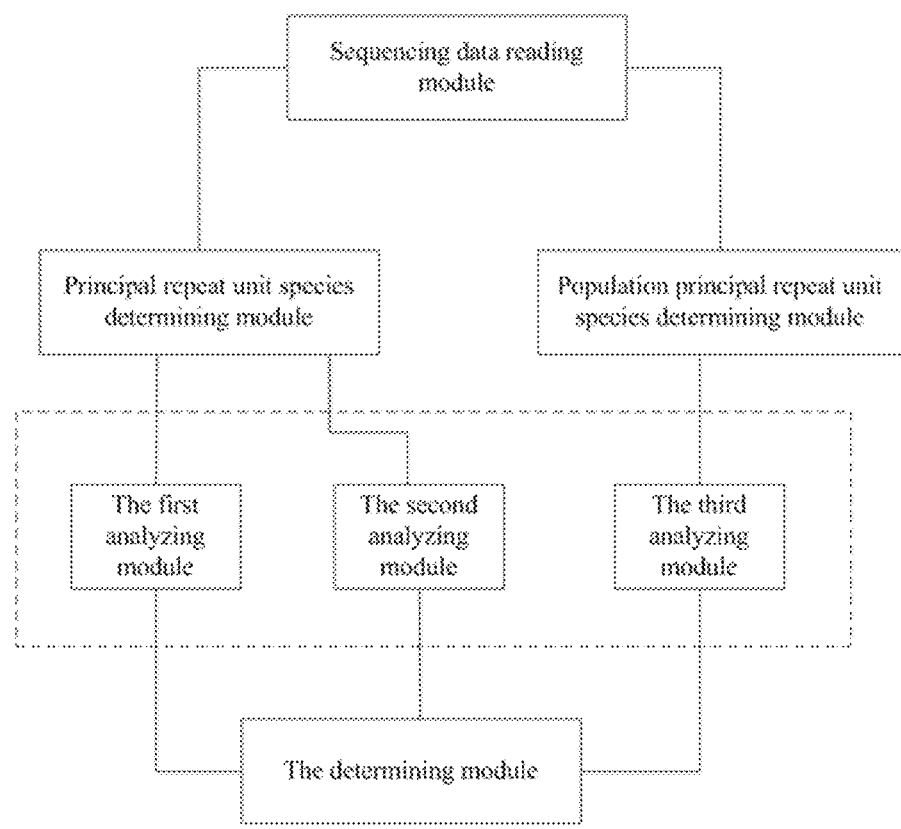
FIG. 2: Module composition diagram of the calculating device provided by the present invention.

The invention will now be further described in detail by way of specific embodiments. However, it will be understood that the following examples are merely illustrative of the invention and should not be construed as limiting the scope of the invention. While specific techniques or conditions are not indicated in the examples, they are carried out according to the techniques or conditions described in the literature of the field or in accordance with the product manuals. The used reagents or instruments which are not provided with the manufacturer information are conventional and commercially-available products. "Computer readable medium" comprises all computer-readable media, with the sole exception being carrier waves.

The term "DNA" as used herein is deoxyribonucleic acid (abbreviated as DNA) which is a double-stranded molecule composed of deoxyribonucleotides. It can form genetic codes to guide organism development and biological function. Its base sequence constitutes genetic information, therefore playing an important role in the diagnosis of genetic diseases.

The term "next generation sequencing technology" as used herein refers to a second generation high throughput sequencing technology and a higher throughput sequencing method developed later. Next-generation sequencing platforms include, but are not limited to, Illumina (Miseq, Hiseq2000, Hiseq2500, Hiseq3000, Hiseq4000, HiseqX Ten, etc.), ABI-Solid, and Roche-454 sequencing platforms. As the sequencing technology continues to evolve, it can be appreciated that other sequencing methods or apparatus can also be used for this test. According to a specific example of the present invention, the nucleic acid tag according to an embodiment of the present invention can be used for at least one of the Illumina, ABI-Solid, and Roche-454 sequencing platforms. Next-generation sequencing technologies, such as Illumina sequencing technology, have the following advantages: (1) High sensitivity: Next-generation sequencing, such as Miseq has high sequencing throughput which can generate up to 15G base data in one experimental process. In the case where the number of sequences is constant, the high data throughput allows for higher sequencing depth for each target of interest so that the low frequency mutations can be detected. In the meanwhile, because of the high sequencing depth, the mutation sites have high coverage leading to a statistically reliable result. (2) High throughput and low cost: With the tag sequence according to an embodiment of the present invention, tens of thousands of samples can be detected by a single sequencing process, thereby greatly reducing the cost.

The term "microsatellite" or "microsatellite region", as used herein, refers to a mononucleotide, dinucleotide, tri-nucleoside, tetranucleotide pentanucleotide or hexanucle-otide repeat consisting of at least two repeat units in a nucleotide sequence and having a length of at least 6 bases. A specific subclass of microsatellites includes homopoly-mers. As used herein, "homopolymer" refers to a microsat-ellite region that is a single nucleotide repeat of at least 6 bases; in other words, at the DNA level, it is a sequence with at least 6 consecutive A, C, T or G bases. More particularly, the individual's genomic DNA (or genomic DNA of the cancer present in the individual) is examined while the microsatellites are determined.

The term "MSI status" as used in the present invention refers to the presence of microsatellite instability (MSI), which is a clonal alteration or somatic alteration of the number of DNA nucleotide repeat units in a microsatellite. The MSI status can be one of three discrete categories: MSI-H, also known as MSI-high, MSI-positive or MSI; MSI-L, also known as MSI-low; and MSS, also known as microsatellite stable, or lack of MSI.

The "mutation", "nucleic acid variation", and "gene varia-tion" in the present invention are in common use. The "SNP" (SNV), "CNV", "insert deletion" (indel), and "structural variation" (SV) in the present invention are defined as usual, but the size of each variation is not particularly limited in the present invention, therefore crossovers among the several variations, such as when the insertion/deletion is a large fragment or even a whole chromosome, belonging to the copy number variation (CNV) or chromosomal aneuploidy also belongs to SV. These types of crossover variations do not prevent the methods and/or apparatus of the present invention being performed to obtain the results described.

The present invention provides a sequencing data analysis method for determining microsatellite instability by analyz-ing data generated with next generation sequencing tech-niques. Specifically, genomic DNA is extracted from cells, body fluids or tissue samples of mammals, such as human, and processed to obtain a fragmented double-stranded DNA as a DNA sample library; then, the DNA sample library is hybridized with a DNA probe library to enrich the MSI-related microsatellite locus fragments from the DNA sample library for next-generation sequencing. The data obtained by sequencing are aligned to the human reference genome GRCh37/hg19 (available from the UCSC website http://genome.ucsc.edu) using common bioinformatics analysis software, and after appropriate process, the number of reads for different repeat units at each microsatellite locus is found out by common bioinformatics analysis software. These results are used as the input signals for the analysis proce-dure provided by the present invention to determine the stability of the microsatellite locus and the microsatellite stability status of the sample.

The present invention first proposes a locus combination for detecting microsatellite instability, including the follow-ing 22 loci: BAT25, BAT26, NR24, NR21, Mono27, NR22, NR27, BAT40, CUL-22, MET-15, ATM-15, RB1-13, NF1-26, DDR-11, FANC-21, MITF-14, PKHD-18, PTK-16, RET-14, CBL-17, PTPN-17, and SMAD-18; The positions of the said microsatellite loci in the genome are shown in Table 1. The genomic locations are determined from the hg19 version of the genomic database; the "chr" and its subsequent number in Table 1 indicate which chromosomes the locus is located in.

The above-mentioned locus combination can effectively solve the risk of misclassifying MSI-H and MSI-L for samples close to the determination threshold, as the cur-rently commercialized MSI detection kit (Promega) can only determine 5 MSI loci (BAT-25, BAT-26, MONO-27, NR-21, NR-24), generating results with poor continuity and large-gapped strata. In the meanwhile, the above-mentioned test method has higher sensitivity than the Promega MSI detec-tion kit for test samples with a low tumor cell content.

When it is necessary to determine whether there is a microsatellite instability status at each locus, methods such as conventional PCR and high-throughput sequencing can be used to test and determine the normal and the test sample. If the number of base repeat units is abnormal, the micro-satellite instability status is determined; preferably, the three determining methods provided by the present invention are used. When it is necessary to determine whether a sample is in the status of MSS, MSI-L, or MSI-H, the proportion can be compared with that of the microsatellite instability in the normal sample, to determine the corresponding status while greater than or less than the set threshold.

The corresponding detection reagents and kits can be designed for detecting the above-mentioned microsatellite locus combination, in which the corresponding probes or primers can be designed according to the sequence of the loci, and/or other control genes and corresponding detection reagents can be added.

In addition, the above microsatellite loci can also be combined with other tumor-associated genes to form a joint biomarker for high-throughput sequencing analysis in order to provide more comprehensive gene profiling. These tumor-associated genes include but are not limited to: AKT1. CTNNB1, FLT3, KRAS, PTPN11, SRC, ALK, EGFR, GNAS, MLH1, RB1, STK11, ATM, ERBB2, HNF1A, MPL, RAD50, TP53, BRAF, ERBB4, IDH1, NRAS, RET, VHL, BRCA1, FBXW7, JAK3, PIK3CA, SMAD4, CDH1, FGFR2, KIT, PTEN, SMARCB1, ABL1, CSF1R, GNA11, JAK2, NOTCH1, SMO, APC, FGFR1, GNAQ, KDR, NPM1, CDKN2, FGFR3, HRAS, MET, and PDGFRA.

To determine the status of a microsatellite locus in a sample based on sequencing results, statistical analysis methods are often performed to compare it with the sequenc-ing results of normal samples, i.e. considering different repeat units present in a certain microsatellite locus of one sample, which have insufficient sensitivity and are prone to missed detection or misjudgment.

The present invention also provides a novel data analysis method for determining the microsatellite instability status based the NGS sequencing data, the main flow of which is: first obtaining the sequencing data primarily for relevant MSI loci in the test sample as well as the normal sample (also referred to as reference) through the NGS, and then processing the sequence information of the corresponding loci obtained by high-throughput sequencing method according to conventional experimental methods, textbooks, probe design methodology, and sequencer manuals, mainly including: DNA extraction of tissue or whole blood samples of each test sample and sample to obtain genomic DNA; fragmentation of the samples with large DNA fragments through ultrasound to mechanically shearing into fragments with 200-350 base pairs; modification of the fragmented DNA molecule such as end-repair, A-tailing, adaptor liga-tion and so on; hybridization of obtained DNA library to a DNA probe library with single-strand biotinylated probes of 120 base in length and then separation of the captured DNA library molecules by streptavidin-coated magnetic beads; sequencing with the illumina next generation sequencer. The data obtained by the sequencing reaction is analyzed by bioinformatics. After the corresponding sequencing information is obtained, the data can be preprocessed by conventional methods to remove adaptor dimers or low-quality reads and so on.

For a certain locus to be tested, it is necessary to obtain reads that can cover the range of the locus. For normal samples, two specific parameters need to be statistically analyzed: the first being the principal repeat unit species and the other being the population principal repeat unit species, which are detailed as follows:

The principal repeat unit species has to be determined for each specific MSI locus within each sample. For example, the SMAD-18 locus has 18 consecutive base A in the reference genomic sequence, but often show 15, 16, 17, 18, or 19 consecutive A repeat base species in normal populations (recorded as the following five repeat units: −3, −2, −1, 0 and 1). Individual healthy human whole blood samples only have two or three of the five repeat units at most, therefore requiring the determination of the principal repeat unit species in each sample. Its calculation is mainly determined by the proportion of the supporting reads. All reads mapped to the locus are obtained, and then classified according to the number of repeated bases. The reads of one species of repeat base number is considered as one class, and the number of reads corresponding to this class is counted. As presented above, in a sample of a normal population, the 16, 17, 18, 19 consecutive A base repeat species may be detected at the SMAD-18 locus. Then, the number of reads for each individual species is added together to obtain the total number of these effective reads ($n_{total}$). Next, the principal repeat unit species among the four is determined by counting the proportion of the reads for each species within the total now, which comprises: taking the repeat unit species with the highest frequency (proportion) of occurrence in an individual sample; if the proportion of the highest repeat unit species is less than 90%, the repeat unit species with the second highest frequency (proportion), the third highest, the forth and so on is added until the total proportion is ≥90%. The following method can be used in the calculation: the repeat units of different repeating base numbers are arranged in descending order according to the numbers of the supporting reads, individually recorded as $n(j)$, $j=1, 2, 3, \ldots$; the percentage of n (j) in the total number of reads are individually calculated as: A $(j)=n(j)/n_{total}*100\%$; with m starting from 1, 2 3 . . . , calculate separately:

$$B = \sum_{j=1}^{m} A(j);$$

If B is ≥90%, the calculation is stopped, and the repeat units with different repeating bases corresponding to A(1) through A(m) are determined as the principal repeat unit species. The above method determines the principal repeat unit species for a specific MSI locus on a particular sample.

The other parameter to be determined is the population principal repeat unit species, which is used to determine the most frequently observed repeat unit species among all normal samples. Similar to the above discussed principal repeat unit species, it is also determined based on the proportion of the number of reads. The difference is that all normal samples are pooled for overall evaluation. First, the sequencing results of all normal groups for a specific MSI locus need to be pooled, followed by the analysis of the sequencing reads spanning this MSI locus. The repeat unit species in all reads are pooled and then the sequencing reads are classified by the number of repeat bases. The reads of one species of repeat base number is considered as one class, and the number of reads corresponding to this class is counted. Then, the number of reads for each individual species is added together to obtain the total number of these effective reads ($n_{total}$). Next, the population principal repeat unit species is determined by counting the proportion of the reads for each species within the total $n_{total}$, which comprises: taking the repeat unit species with the highest frequency (proportion) of occurrence in an individual sample; if the proportion of the highest repeat unit species is less than 90%, the repeat unit species with the second highest frequency (proportion), the third highest, the forth and so on is added until the total proportion is ≥90%. The following method can be used in the calculation: the repeat units of different repeating base numbers are arranged in descending order according to the numbers of the supporting reads, individually recorded as $n(j)$, $j=1, 2, 3, \ldots$; the percentage of n (j) in the total number of reads are individually calculated as: A $(j)=n(j)/n_{total}*100\%$; with m starting from 1, 2 3 . . . , calculate separately:

$$B = \sum_{j=1}^{m} A(j);$$

If B is ≥90%, the calculation is stopped, and the repeat units with different repeating bases corresponding to A(1) through A(m) are determined as the principal repeat unit species. The above method determines the principal repeat unit species for a specific MSI locus on a particular sample.

After obtaining the results to the two parameters above, it is necessary to analyze the sequencing information of this MSI locus. Here, any one of the following three determination methods can be used for the determination. To further improve the detection sensitivity, any two of the following three methods can be adopted. If the condition is satisfied for either method, the locus is determined as a microsatellite instability one; preferably, all three determination methods are used simultaneously. If the condition for any one of the methods is satisfied, the locus is determined as a microsatellite unstable. The present invention found that the combination of the three methods does not cause reduction in specificity of the determination result. The details of these three methods are described as follows:

The first determining method is aimed to limit the number of principal repeat unit species. While this method is used in the test sample, those loci with significantly higher number of principal repeat unit species can be marked as unstable, making the overall determining result more consistent with that of the 5-loci Promega kit. It is necessary to obtain the principal repeat unit species in each normal sample before this method is used, and then separately count the number of these principal repeat unit species ($N_i$). For example, if the principal repeat unit species detected at the SMAD-18 locus in a normal sample are with 18 and 19 consecutive A bases, the number of principal repeat unit species for this sample at this locus is 2. After the number of the principal repeat unit species of one locus is obtained from all samples, statistical analysis is performed to calculate the mean value [mean($N_i$)] and standard deviation [sd($N_i$)] of the set $N_i$. Next, the number of the principal repeat unit species at this locus of the test sample is analyzed in a similar way. For example, if the repeat units of 15, 17, 18, and 19 repetitive bases at the SMAD-18 locus in a test sample are determined as the principal repeat unit species, then the number of the principal repeat unit species for this test sample at this locus is 4. If the number of species in the test sample is greater than the value mean($N_i$)+x*sd($N_i$), the MSI locus in the test sample is considered as unstable; wherein the x in the equitation is a coefficient for standard deviation, preferably 3. Repeat the process for all MSI loci.

The second determining method is aimed to limit the occurrence of principal repeat unit species in the test sample that is not present in the normal samples. The present invention found that at some loci, determination of the sample with this feature as being unstable can improve the overall sensitivity. This determination method also relies on the above-mentioned principal repeat unit species. After the principal repeat unit species in all normal samples are obtained, the test sample is analyzed. If one or more principal repeat unit species in the test sample have never appeared in any normal sample, the MSI locus in the test sample is determined as unstable. This can avoid some false negative results, and hence increasing the sensitivity of the determining method.

The third determining method is aimed to limit the proportion of the population principal repeat unit species in the sample to a specific range, not too high or too low. The present invention found that adoption of this method suppresses false negatives and improves the detection sensitivity. Briefly, the process of this method is: identifying the population principal repeat unit species; followed by determining the presence of these species in every normal sample; If present, the number of reads corresponding to these species (n) are counted, as well as and the number of reads for all sequencing reads spanning this MSI locus ($n_{total}$), to compute the proportion of n in the now. For example, at PTK-16 locus, firstly, the number of sequencing reads corresponding to the locus from 100 normal human samples is counted, and 18696 reads are obtained in all-50,000 sequencing reads. Among the reads in which repeat units of 12, 13, 14, 15, 16, 17, 18, 19, 20 repeat bases are found (labeled respectively as −4, −3, −2, −1, 0, 1 2, 3, 4), 17013 reads belong to the 16 repeat base species, accounting for 91% of all reads. The 16 base species is thus determined to be the population principal repeat unit type at this MSI locus; Then, the proportion of the 16-base species is calculated individually for the sequencing data of the 100 normal samples, as well as the total number of reads. For example, for the sequencing results of a normal individual A, a total of 100 reads are mapped to the PTK-16 locus, among which 5, 5, 60, and 30 reads correspond to the 14, 15, 16, and 17 base species respectively, resulting in a proportion of the 16-base species for A as 60/100=0.6. Similarly, the proportion of the 16-base species for another normal individual B is 20/100=0.2. Therefore, individual proportions can be obtained for the population of 100, presented as a set containing 0.6, 0.2 and so on. Next, the distribution of these 100 proportion values is analyzed to calculated the median Q2 ($R_i$), the first quartile Q1 ($R_i$) and the third quartile Q3 ($R_i$). The proportion of this 16-base species at this MSI locus within a test sample ($RT_i$) is calculated following the same logic. If the RT satisfies the following conditions, this MSI locus in the test sample is determined as unstable unstable:

$RT_i > Q2(R_i)+1.5*(Q3(R_i)-Q1(R_i))$ or $RT_i < Q2(R_i)-1.5*(Q3(R_i)-Q1(R_i))$.

After applying the above described calculation for all MSI loci, the stability of each MSI locus within the test sample may be determined. Consequently, the microsatellite stability of the test sample can be in turn determined based the proportion of unstable MSI loci. A comparison can be made between the proportion of normal samples and that of samples with known microsatellite stability status, which yield threshold values to distinguish MSS, MSI-L or MSI-H of the test sample j.

The above method is for non-therapeutic and non-diagnostic purposes, which is only used to determine whether the sample has microsatellite instability and prevent the occurrence of false negative outcomes. However, the occurrence of MSI phenomenon is not substantially related to the clinical characteristics of the cancer sample.

Based on the above method, the calculation method may be composed of a conventional calculation module to form a calculation device, or may be written into an executable program and recorded in a memory. The present invention also provides a computer storage medium storing the above-described calculation method program, and a computer system in which the above method can be operated.

Example 1 Initial Screening of Loci

The present invention demonstrates the application of the analysis procedure and the MSI locus screening method by the following examples. We performed high-throughput sequencing of tumor tissue samples from 2000 Chinese individuals with solid tumors and corresponding whole-blood negative control samples. The targeted genomic areas detected were the entire exonic regions of 422 cancer-related genes, and some intronic regions frequently displaying gene fusions. The detection used liquid phase capture to enrich the target DNA. The sequencing process was a common next-generation sequencing method, briefly described as follows: genomic DNA extraction was performed on tissue samples and whole blood samples of each patient; ultrasonication was used to mechanically break the large DNA fragments into 200-350 bp in length; operations such as end-repair, A-tailing, and library adapter ligation were performed for the fragmented DNA molecules; the obtained DNA library was then hybridized with biotin-labeled DNA probes of 120 bp in length, followed by the separation with streptavidin-coated magnetic beads; the sequencing was performed on an illumina next-generation sequencer. The data obtained by the sequencing reaction were analyzed by bioinformatics, and 96 loci with single-base repeat units composed of >10 base pairs which showed insertion/deletion mutations in the tumor samples were found within the targeted regions.

Information on the 96 loci with single-base repeat units and insertion/deletion mutations found by this embodiment:

TABLE 2

The information of the initially-screened 96 loci

| Locus No. | MSI locus name | Repeat unit (number) | Genomic location (Human Hg19) |
|---|---|---|---|
| MS-1 | BAT-25 | T(25) | chr4: 55,598,212-55,598,236 |
| MS-2 | BAT-26 | A(27) | chr2: 47,641,560-47,641,586 |
| MS-3 | NR-24 | T(23) | chr2: 95,849,362-95,849,384 |
| MS-4 | NR-21 | T(21) | chr14: 23,652,347-23,652,367 |
| MS-5 | Mono-27 | A(27) | chr2: 39,536,690-39,536,716 |
| MS-6 | NR-22 | T(21) | chr11: 125,490,766-125,490,786 |
| MS-7 | NR-27 | A(26) | chr11: 102,193,509-102,193,534 |
| MS-8 | BAT-40 | T(37) | chr1: 120,053,341-120,053,377 |
| MS-9 | CUL-22 | A(22) | chr2: 225,422,601-225,422,622 |
| MS-10 | MET-15 | T(15) | chr7: 116,409,676-116,409,690 |
| MS-11 | ATM-15 | T(15) | chr11: 108,114,662-108,114,676 |

TABLE 2-continued

The information of the initially-screened 96 loci

| Locus No. | MSI locus name | Repeat unit (number) | Genomic location (Human Hg19) |
|---|---|---|---|
| MS-12 | RB1-13 | T(13) | chr13: 48,954,160-48,954,172 |
| MS-13 | NF1-26 | T(26) | chr17: 29,559,062-29,559,087 |
| MS-14 | DDR-11 | A(11) | chr1: 162,736,822-162,736,832 |
| MS-15 | FANC-21 | A(21) | chr3: 10,076,009-10,076,029 |
| MS-16 | MITF-14 | T(14) | chr3: 69,988,438-69,988,451 |
| MS-17 | PKHD-18 | A(18) | chr6: 51,503,598-51,503,615 |
| MS-18 | PTK-16 | A(16) | chr8: 141,754,889-141,754,904 |
| MS-19 | RET-14 | T(14) | chr10: 43,595,837-43,595,850 |
| MS-20 | CBL-17 | T(17) | chr11: 119,144,792-119,144,808 |
| MS-21 | PTPN-17 | T(17) | chr12: 112,893,676-112,893,692 |
| MS-22 | SMAD-18 | A(18) | chr18: 45,395,846-45,395,863 |
| MS-23 | Can-0001 | C(14) | chr1: 61872214-6187232 |
| MS-24 | Can-0002 | A(16) | chr1: 32027857-22027876 |
| MS-25 | Can-0003 | T(22) | chr1: 38304468-38304493 |
| MS-26 | Can-0004 | T(17) | chr1: 39900057-39900077 |
| MS-27 | Can-0005 | A(15) | chr1: 115238015-115238033 |
| MS-28 | Can-0006 | T(16) | chr1: 118501389-118501408 |
| MS-29 | Can-0007 | A(15) | chr1: 220800160-220800178 |
| MS-30 | Can-0008 | A(16) | chr1: 231094049-231094068 |
| MS-31 | Can-0009 | T(14) | chr10: 26802632-26802649 |
| MS-32 | Can-0010 | A(16) | chr10: 26825150-26825169 |
| MS-33 | Can-0011 | A(13) | chr10: 74906121-74906137 |
| MS-34 | Can-0012 | T(16) | chr11: 43419086-43419105 |
| MS-35 | Can-0013 | T(15) | chr11: 83500592-83500610 |
| MS-36 | Can-0014 | T(16) | chr11: 93463144-93463163 |
| MS-37 | Can-0015 | T(19) | chr11: 120348127-120348149 |
| MS-38 | Can-0016 | T(12) | chr12: 7868864-7868879 |
| MS-39 | Can-0017 | T(17) | chr12: 28412397-28412417 |
| MS-40 | Can-0018 | A(16) | chr12: 30881487-30881506 |
| MS-41 | Can-0019 | T(13) | chr12: 56999548-56999564 |
| MS-42 | Can-0020 | T(15) | chr12: 101779989-101780007 |
| MS-43 | Can-0021 | T(22) | chr14: 50361170-50361195 |
| MS-44 | Can-0022 | T(18) | chr15: 32982041-32982062 |
| MS-45 | Can-0023 | A(16) | chr15: 41571407-41571426 |
| MS-46 | Can-0024 | A(16) | chr15: 78838789-78838808 |
| MS-47 | Can-0025 | A(24) | chr15: 90296269-90296296 |
| MS-48 | Can-0026 | A(18) | chr16: 89807043-89807064 |
| MS-49 | Can-0027 | A(18) | chr17: 2238740-2238761 |
| MS-50 | Can-0028 | A(16) | chr17: 42945540-42945559 |
| MS-51 | Can-0029 | T(21) | chr17: 45754177-45754196 |
| MS-52 | Can-0030 | T(16) | chr19: 6833161-6833180 |
| MS-53 | Can-0031 | A(13) | chr19: 12128922-12128938 |
| MS-54 | Can-0032 | T(16) | chr2: 43054033-43054052 |
| MS-55 | Can-0033 | A(18) | Chr13: 20041492-20041513 |
| MS-56 | Can-0034 | A(16) | chr2: 97683391-97683410 |
| MS-57 | Can-0035 | T(14) | chr2: 107096580-107096597 |
| MS-58 | Can-0036 | T(14) | chr2: 162876812-162876829 |
| MS-59 | Can-0037 | A(17) | chr2: 175614907-175614927 |
| MS-60 | Can-0038 | A(13) | chr2: 179988394-179988410 |
| MS-61 | Can-0039 | T(19) | chr2: 183995114-183995136 |
| MS-62 | Can-0040 | A(16) | chr2: 213872835-213872854 |
| MS-63 | Can-0041 | T(22) | chr2: 219103312-219103337 |
| MS-64 | Can-0042 | T(18) | chr20: 4706781-4706802 |
| MS-65 | Can-0043 | A(16) | chr20: 10627472-10627491 |
| MS-66 | Can-0044 | A(16) | chr20: 31975061-31975080 |
| MS-67 | Can-0045 | T(23) | chr20: 44756942-44756968 |
| MS-68 | Can-0046 | T(15) | chr20: 48562796-48562814 |
| MS-69 | Can-0047 | A(16) | chr21: 45475457-45475476 |
| MS-70 | Can-0048 | T(18) | chr22: 42993785-42993806 |
| MS-71 | Can-0049 | T(14) | chr3: 15288741-15288758 |
| MS-72 | Can-0050 | T(19) | chr3: 33893928-33893950 |
| MS-73 | Can-0051 | T(13) | chr3: 62267212-62267228 |
| MS-74 | Can-0052 | A(17) | chr4: 8176743-8176763 |
| MS-75 | Can-0053 | T(15) | chr4: 76721670-76721688 |
| MS-76 | Can-0054 | A(20) | chr4: 99877751-99877774 |
| MS-77 | Can-0055 | T(17) | chr4: 108931132-108931152 |
| MS-78 | Can-0056 | A(14) | chr4: 122053909-122053926 |
| MS-79 | Can-0057 | A(13) | chr4: 169325281-169325297 |
| MS-80 | Can-0058 | T(30) | chr5: 68548320-68548353 |
| MS-81 | Can-0059 | A(20) | chr5: 108679800-108679823 |
| MS-82 | Can-0060 | T(21) | chr6: 6167557-6167581 |
| MS-83 | Can-0061 | T(17) | chr6: 17779972-17779992 |
| MS-84 | Can-0062 | A(15) | chr6: 137325900-137325918 |
| MS-85 | Can-0063 | A(23) | chr7: 23545203-23545229 |
| MS-86 | Can-0064 | T(13) | chr7: 28534392-28534408 |
| MS-87 | Can-0065 | T(16) | chr7: 74536838-74536857 |
| MS-88 | Can-0066 | A(19) | chr7: 152351281-152351303 |
| MS-89 | Can-0067 | T(13) | chr8: 109462214-109462230 |
| MS-90 | Can-0068 | T(21) | chr9: 5738544-5738568 |
| MS-91 | Can-0069 | A(13) | chr9: 97555227-97555243 |
| MS-92 | Can-0070 | A(13) | chrX: 3539375-3539391 |
| MS-93 | Can-0071 | T(14) | chrX: 44918220-44918237 |
| MS-94 | Can-0072 | T(23) | chrX: 48186296-48186322 |
| MS-95 | Can-0073 | T(30) | chrX: 76709762-76709795 |
| MS-96 | Can-0074 | A(18) | chrX: 77264513-77264534 |

To further resolve the problems presented by the Promega MSI analysis system, i.e. results with poor continuity and large-gaped gradients as a consequence of only evaluating 5MSI loci (BAT 25, BAT-26, MONO-27, NR-21, NR-24), we enrolled 100 healthy human whole blood samples and 163 clinical samples of colorectal cancer that received the Promega test, breaking down into 133 MSS, 6MSI-L, and 24 MSI-H samples. The following screening conditions were performed on the above 96 candidate loci: 1. The locus should be well covered, and the sequencing depth of the covered locus should reach 20% of the average depth of the whole sample. 2. In normal samples, the repeat unit species with the highest read proportion should constitute no less than 60%/of all covered loci. 3. In normal samples, at least 80%/of the reads of the covered locus should not contain the insertion or deletion mutations of >1 base pair deviating from the repeat unite type with the highest read proportion. 4. This locus was determined as stable in more than 80% of MSS samples (based on immunohistochemistry or Promega PCR). 5. This locus was determines as unstable in more than 80% of MSI-H samples (based on immunohistochemistry or Promega PCR). A total of 22 loci met these conditions after the screening, and are listed in Table 1. These 22 loci are consistent with those determined by the 5 loci Promega kit in both normal and patient samples, and the detection gradient for the Promega kit is further accurately subdivided.

Example 2 Data Analysis of Microsatellite Instability Status

The 100 healthy human whole blood samples in Example 1, and 163 clinical samples of colorectal cancer which were tested by Promega kit were used for sequencing of microsatellite loci, and the sequencing process was performed in the illumina next generation sequencer.

First, the sequencing data of the normal and the patient samples were analyzed to found the reads spanning the 22 MSI loci, and then these reads are classified and counted according to the number of single base repeats in these microsatellite loci. The principal repeat unit species of the normal and patient samples at each locus, and the population principal repeat unit species of all normal samples at each locus are determined. Then, the mean and standard deviation of the principal repeat unit species on the 22 MSI loci (as shown in Table 3), and the median Q2, the first quartile Q1 ($R_i$) and the third quartile Q3 ($R_i$) of the population principal repeat unit species in all normal samples on the 22 MSI loci, were calculated (as shown in Table 4).

TABLE 3

The mean and standard deviation of the principal repeat unit species

| Locus name | Principal repeat unit species | |
|---|---|---|
| | Mean | Standard deviation |
| BAT-25 | 5.47 | 1.314 |
| BAT-26 | 5.97 | 1.352 |
| NR-24 | 4.63 | 1.220 |
| NR21 | 5.58 | 1.241 |
| MONO27 | 5.02 | 1.497 |
| NR22 | 2.38 | 1.144 |
| NR27 | 4.44 | 1.122 |
| BAT40 | 3.37 | 0.761 |
| CUL-22 | 2.49 | 0.823 |
| MET-15 | 4.76 | 1.102 |
| ATM-15 | 3.59 | 0.712 |
| RB1-13 | 4.74 | 1.151 |
| NF1-26 | 4.23 | 1.188 |
| DDR-11 | 3.45 | 0.833 |
| FANC-21 | 4.11 | 0.815 |
| MITF-14 | 4.75 | 1.290 |
| PKHD-18 | 3.82 | 0.845 |
| PTK-16 | 3.77 | 0.777 |
| RET-14 | 5.65 | 1.266 |
| CBL-17 | 4.46 | 1.009 |
| PTPN-17 | 4.98 | 1.128 |
| SMAD-18 | 2.86 | 0.450 |

TABLE 4

The median, the first quartile and the third quartile of the population principal repeat unit species

| LOCUS NAME | Population principal repeat unit species | | |
|---|---|---|---|
| | Median | The first quartile | The third quartile |
| BAT-25 | 0.933 | 0.909 | 0.963 |
| BAT-26 | 0.916 | 0.863 | 0.952 |
| NR-24 | 0.924 | 0.897 | 0.948 |
| NR21 | 0.945 | 0.859 | 0.990 |
| MONO27 | 0.885 | 0.827 | 0.936 |
| NR22 | 0.968 | 0.927 | 0.990 |
| NR27 | 0.986 | 0.930 | 0.990 |
| BAT40 | 0.937 | 0.906 | 0.960 |
| CUL-22 | 0.960 | 0.943 | 0.976 |
| MET-15 | 0.860 | 0.830 | 0.904 |
| ATM-15 | 0.868 | 0.844 | 0.893 |
| RB1-13 | 0.884 | 0.852 | 0.914 |
| NF1-26 | 0.877 | 0.841 | 0.912 |
| DDR-11 | 0.868 | 0.834 | 0.907 |
| FANC-21 | 0.927 | 0.885 | 0.967 |
| MITF-14 | 0.845 | 0.781 | 0.887 |
| PKHD-18 | 0.916 | 0.879 | 0.955 |
| PTK-16 | 0.915 | 0.891 | 0.954 |
| RET-14 | 0.909 | 0.858 | 0.968 |
| CBL-17 | 0.909 | 0.863 | 0.945 |
| PTPN-17 | 0.944 | 0.912 | 0.973 |
| SMAD-18 | 0.926 | 0.857 | 0.981 |

The data of the patient samples were analyzed according to the above three analyzing modules, and the results were compared with those of the Promega kit.

Figure 3:
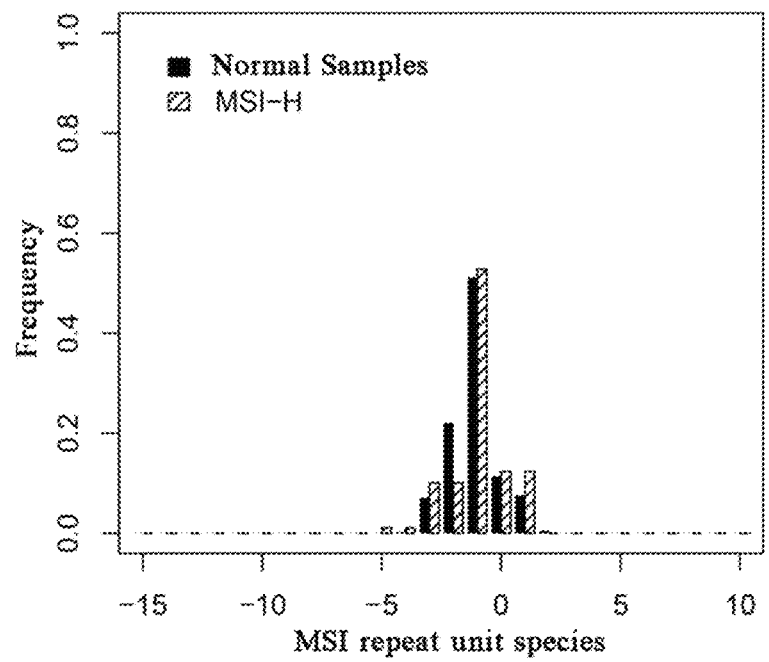
FIG. 3: Proportional distribution of repeat unit species with different numbers of repeating base pair at the SMAD-18 locus in the normal sample and the MSI-H sample.

As shown in FIG. 3, the pooled analysis of 100 healthy human whole blood samples showed that the SMAD-18 locus had five common repeat unit types, −3, −2, −1, 0 and 1, but an individual normal sample only had two or three of these common types. One of the MSI-H samples had all five repeat unit types at the SMAD-18 locus, indicating the locus being unstable. If the locus is analyzed only by the two determining conditions of "the presence of principal repeat unit species never detected in normal" (the second analyzing module) and the "the proportion of the population principal repeat unit species" (the third analyzing module) provided by the present invention, this locus would be misjudged as stable. Therefore, it is necessary to use "the number of principal repeat unit species" (the first analyzing module of determination) for comparison.

Figure 4:
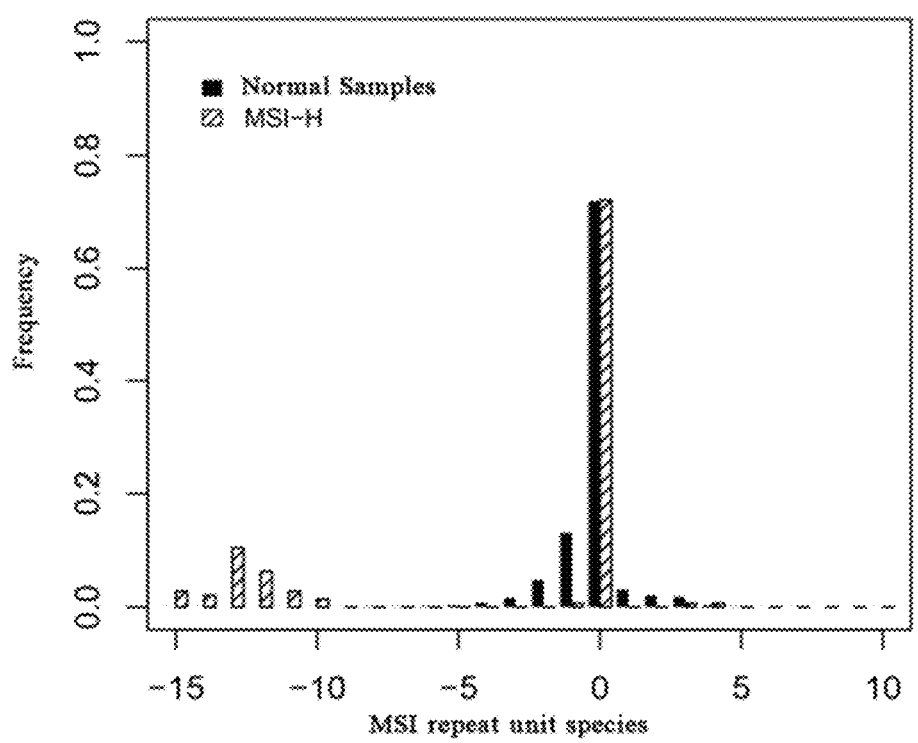
FIG. 4: Proportional distribution of repeat unit species with different numbers of repeating base pair at the NF1-26 locus in the normal sample and the MSI-H sample.

As shown in FIG. 4, pooled analysis of 100 healthy human whole blood samples showed that the NF1-26 locus had 9 commons repeat unit types from −4 to 4. One MSI-H sample also showed multiple different repeat units in NF1-26 locus including the unusual types from −15 to −10 which had never appeared in the normal samples, suggesting this locus of this MSI-H sample is unstable. If the locus was analyzed only by the two determining conditions of "the number of principal repeat unit species" and "the proportion of the population principal repeat unit species" provided by the present invention, this locus would be misjudged as stable. Therefore, it is necessary to use the method of "the presence of principal repeat unit species never detected in normal" to make the correct determination.

Figure 5:
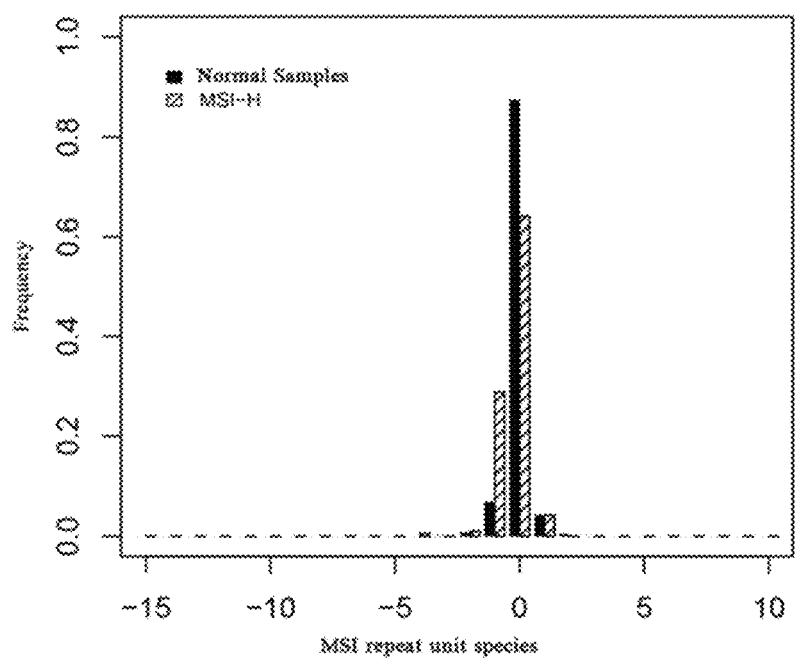
FIG. 5: Proportional distribution of repeat unit species with different numbers of repeating base pair at the PTK-16 locus in the normal sample and the MSI-H sample.

As shown in FIG. 5, the pooled analysis of 100 healthy human whole blood samples showed that the PTK-16 locus had three common repeat unit types, −1, 0, and 1, among which 0 is the population principal repeat unit species. The proportion of this population principal repeat unit species for one MSI-H sample at the PTK-16 locus was only 60%, indicating this locus for this sample being unstable. If this locus is analyzed only by the two determining conditions of "the number of principal repeat unit species" and "the presence of principal repeat unit species never detected in normal" proposed by the present invention, this locus will be misjudged as stable. Therefore, it is necessary to adopt the module of "the proportion of the human-population-predominate repeat unit type" for determination.

Example 3 Microsatellite Instability Analysis with Locus Combinations

In order to demonstrate the superiority of the biomarker with a combination of 22 microsatellite instability loci provided by the present invention, the 22 loci obtained by methods of the present invention, were compared to 22 randomly selected loci among the remaining 96 candidate loci, to exam the accuracy of determining the patients' microsatellite instability.

Figure 6:
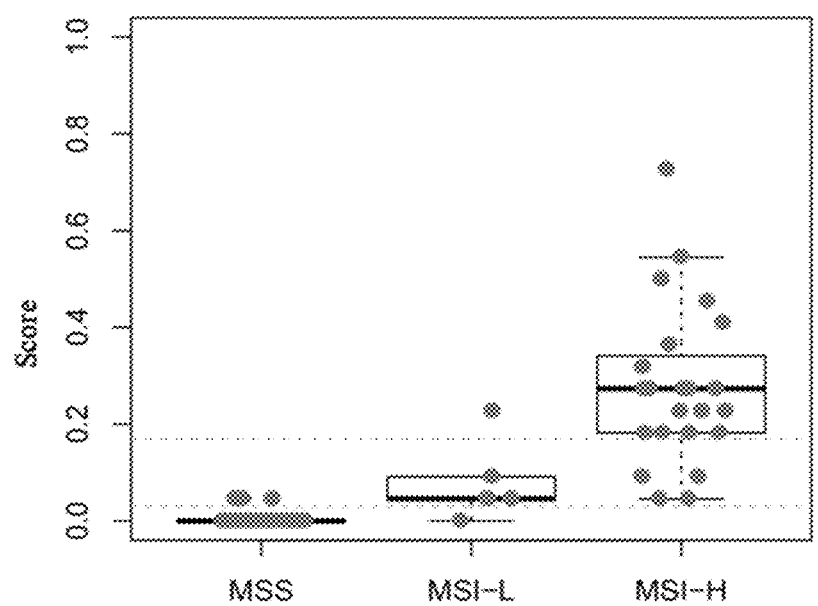
FIG. 6: Box plot of the results from the control experiment 1 of Example 3 for determining the microsatellite instability.

Control Experiment 1: FIG. 6 shows the results obtained using only one determining condition of "number of principal repeat unit species" with randomly selected 22 microsatellite instability loci (MSI locus number 39, 88, 43, 34, 25, 56, 63, 69, 42, 32, 28, 45, 59, 98, 44, 50, 85, 99, 67, 53, 52, and 66 of Table 2). The classification of MSS, MSI-L, and MSI-H in the figure was based on the results of the Promega kit, and therein each data point is a clinical sample of the 163 tested by the Promega microsatellite test kit, including 133 MSS, 6 MSI-L, and 24 MSI-H. The proportion mentioned in the figure is the final proportion of unstable MSI loci obtained by the MSI determining methods provided by the present invention. As shown in the figure, it is apparent that the threshold between MSS and MSL-L is very ambivalent, causing difficulty to distinguish these two classifications. It is also indistinguishable from MSI-L and MSI-H, and there is a misjudgment of at least one MSI-L sample and four MSI-H samples.

Figure 7:
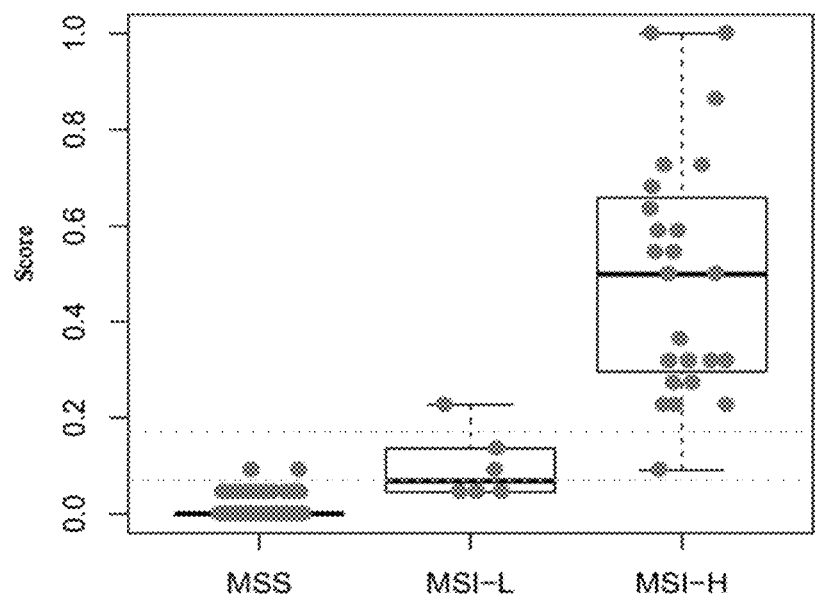
FIG. 7: Box plot of the results from the control experiment 2 of Example 3 for determining the microsatellite instability status.

Control Experiment 2: FIG. 7 shows the results obtained using three determining conditions of "the number of principal repeat unit species", "the presence of principal repeat unit species never detected in normal", and "the proportion of the population principal repeat unit specits" with randomly selected 22 microsatellite instability loci (MSI locus number 39, 88, 43, 34, 25, 56, 63, 69, 42, 32, 28, 45, 59, 98, 44, 50, 85, 99, 67, 53, 52, and 66 of Table 2). The test sensitivity is significantly improved compared with that for FIG. 6. However, MSI-L and MSI-H remain difficult to be distinguished, and there is a misjudgment of at least one MSI-L sample and one MSI-H.

Control Experiment 3: the results obtained using three determining conditions of "the number of principal repeat unit species", "the presence of principal repeat unit species never detected in normal", and "the proportion of the population principal repeat unit specits" with randomly selected 22 microsatellite instability loci (MSI locus number 28, 69, 43, 38, 70, 31, 35, 81, 54, 29, 73, 59, 32, 88, 64, 42, 62, 53, 57, 83, 30, and 76 of Table 2).

Control Experiment 4: the results obtained using three determining conditions of "the number of principal repeat unit species", "the presence of principal repeat unit species never detected in normal", and "the proportion of the population principal repeat unit specits" with randomly selected 22 microsatellite instability loci (MSI locus number 76, 41, 43, 39, 99, 48, 42, 54, 33, 46, 35, 32, 79, 57, 49, 90, 58, 77, 88, 81, 82, and 74 of Table 2).

Figure 8:
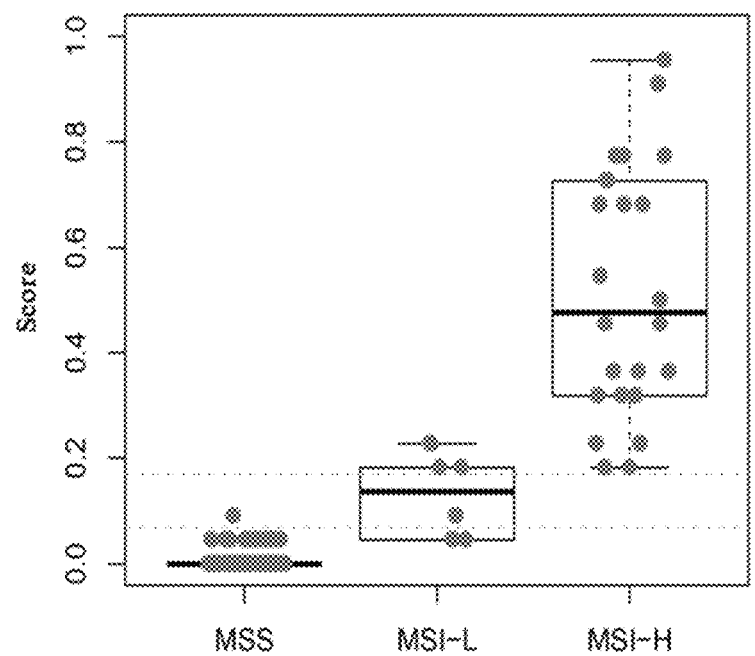
FIG. 8: Box plot of the results from the control experiment 3 of Example 3 for determining the microsatellite instability status.

Control Experiment 5: FIG. 8 shows the results obtained using only one determining conditions of "the number of principal repeat unit species", with 22 microsatellite instability loci determined by the MSI locus screening protocol provided by the present invention. Although the test sensitivity is further improved than those shown in FIG. 6 and FIG. 7, the MSI-L and MSI-H samples close to the determination threshold cannot be clearly distinguished, and there is a high risk of misjudgment to the sample close to the determining threshold.

Figure 9:
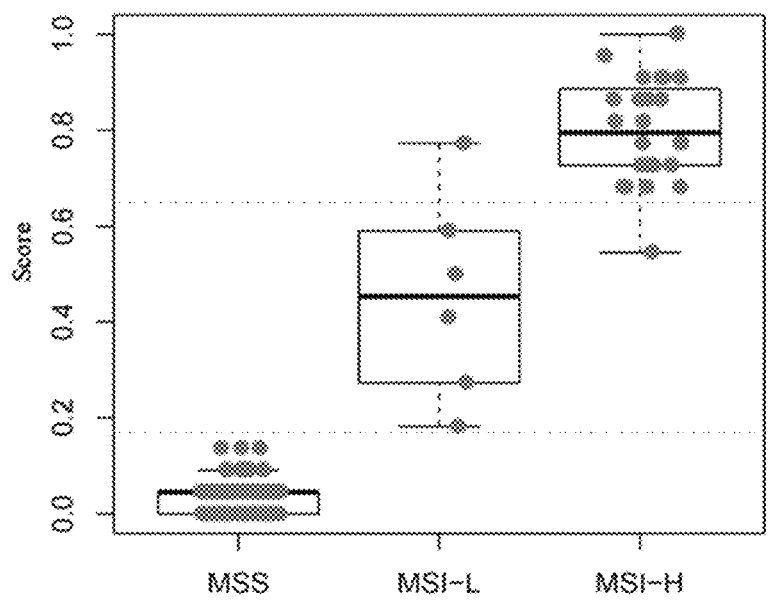
FIG. 9: Box plot of the results from Example 3 for determining the microsatellite instability status using methods provided by the present invention.

Experiment of the method of the present invention: FIG. 9 shows the results obtained using three determining conditions of "the number of principal repeat unit species", "the presence of principal repeat unit species never detected in normal", and "the proportion of the population principal repeat unit specits" with 22 microsatellite instability loci determined by the MSI locus screening protocol provided by the present invention. The test sensitivity is extremely high while maintaining a very high specificity for MSS samples. If the final scores of 0.18 and 0.65 are used as the determining thresholds, the results using the determining method provided by the present invention achieves a 98.8 accuracy with that by the Promega PCR microsatellite test. The samples that did not have the same conclusions were 1 case of MSI-L and 1 case of MSI-H, which are close to the determining thresholds. Misjudgment by Promega test for these two discordant samples remains possible.

Determining thresholds used for above experiments are summarized as follows:

TABLE 5

Microsatellite instability determination results

| | Threshold | Number of MSS | Number of MSI-L | Number of MSI-H | Accuracy compared to Promega Kit |
|---|---|---|---|---|---|
| Control experiment 1 | 0.03, 0.17 | 130 | 12 | 21 | 93.3% |
| Control experiment 2 | 0.07, 0.17 | 134 | 5 | 24 | 95.7% |
| Control experiment 3 | 0.08, 0.19 | 122 | 11 | 30 | 90.1% |
| Control experiment 4 | 0.06, 0.22 | 127 | 13 | 23 | 91.4% |
| Control experiment 5 | 0.07, 0.17 | 134 | 1 | 27 | 96.3% |
| Experiment with methods of the present invention | 0.18, 0.65 | 133 | 6 | 24 | 98.8% |

Example 4A Dilution Series Test on DNA Samples of HCT-116 Cell Line

Since the Promega assay is based on PCR and the first generation Sanger sequencing method, the sensitivity of its detection technique is lower than that of the second generation sequencing method described in the present invention. In practice, biopsy samples obtained from solid tumor lesions often contain a high proportion of normal cells, while the percentage of tumor cells (also known as tumor cell content) is very low. In order to demonstrate that the analytical method of the present invention also has extremely high test sensitivity in samples with low tumor cell content, the present application conducted a gradient dilution test on a MSI-H positive sample.

The HCT-116 cell line is a widely used and studied line of colorectal cancer cells. A large number of scientific data indicate that it has high frequency of microsatellite instability (MSI-H), and most of the microsatellite loci on its genome appear microsatellite instability. In Example 4, genomic DNA extracted from the normal human lymphocyte line GM18535 was used as a dilute vehicle, and the genomic DNA extracted from the HCT-116 cell line was diluted to 5%, 10%, 15%, 20%, 30%, 50%, and 100% by mass. The mixed DNA samples are individually tested using the test method of the present invention and the Promega kit respectively, and the obtained results are as follows:

TABLE 6

Test results of gradient dilution of HCT-116 cell line genomic DNA samples

| Proportion of HCT-116 genomic DNA (by mass) | Number of unstable loci MSI determined by Promega kit | MSI Status determined by Promega kit | Proportion of unstable MSI loci determined by the present invention | MSI status determined by the present invention |
| --- | --- | --- | --- | --- |
| 100% | 5 | MSI-H | 0.91 | MSI-H |
| 50% | 5 | MSI-H | 0.91 | MSI-H |
| 30% | 4 | MSI-H | 0.91 | MSI-H |
| 20% | 2 | MSI-H | 0.77 | MSI-H |
| 15% | 1 | MSI-L | 0.73 | MSI-H |
| 10% | 0 | MSS | 0.73 | MSI-H |
| 5% | 0 | MSS | 0.55 | MSI-L |

It can be noted that Promega is unable to accurately determine the microsatellite stability of the sample when the tumor cell abundance is less than 20%, while the test of the present invention can accurately determine the microsatellite status of the sample even the tumor cell abundance is as low as 10%.

What is claimed is:

1. A method for analyzing sequencing data of microsatellite instability, comprising the following steps:

S1: performing Next Generation Sequencing (NGS) on a plurality of test samples and a plurality of normal samples to obtain sequencing data spanning Microsatellite Instability (MSI) locus to be determined in the plurality of test samples and the plurality of normal samples to identify a stable or unstable status of each MSI locus in each of the plurality of test samples and the plurality of normal samples to provide a genomic locus suitable for use as a microsatellite instability indicator;

S2: for the sequencing data obtained in the step S1, using any one of the following three criteria for analysis, and if any of the three criteria is satisfied, then determining the MSI locus of a test sample is unstable;

S2-1: according to the sequencing data obtained in the step S1, calculating a plurality of principal repeat unit species at the MSI locus for each of the plurality of test samples and each of the plurality of normal samples; a tallying number ($N_i$) of the plurality of principal repeat unit species in the each of the plurality of normal samples, and calculating mean value [mean($N_i$)] of the $N_i$ and standard deviation [sd($N_i$)]; if a number of the plurality of principal repeat unit species at the MSI locus in the test sample is larger than mean($N_i$)+x*sd($N_i$), then determining the MSI locus in the test sample is an unstable microsatellite locus, wherein x is a coefficient of standard deviation, and x=3;

S2-2: according to the sequencing data obtained in the step S1, calculating the plurality of principal repeat unit species at the MSI locus of the each of the plurality of test samples and the each of the plurality of normal samples; and if the plurality of principal repeat unit species that have not appeared in any of the plurality of normal samples are found in the test sample at the MSI locus, then determining the MSI locus in the test sample is the unstable microsatellite locus; and S2-3: according to the sequencing data obtained in the step S1, pooling all of the plurality of normal samples as a whole, calculating a plurality of population principal repeat unit species in all of the plurality of normal samples, and then calculating a proportion of the plurality of population principal repeat unit species in the each of the plurality of normal samples, performing statistical analysis according to the proportion to obtain a distribution reference set and calculate median [Q2($R_i$)], first quartile [Q1($R_i$)], and third quartile [Q3($R_i$)] of the proportion, and calculating a proportion ($RT_i$) of the plurality of population principal repeat unit species in the each of the plurality of test samples; and if $RT_i > Q2(R_i)+1.5*(Q3(R_i)-Q1(R_i))$ or $RT_i < Q2(R_i)-1.5*(Q3(R_i)-Q1(R_i))$, then determining that the MSI locus in the test sample is the unstable microsatellite locus.

2. The method for analyzing the sequencing data of the microsatellite instability according to claim 1, wherein the plurality of principal repeat unit species in the step S2-1 and the step S2-2 is calculated by the following steps:

S3-1: according to a sequencing result of one of a plurality of samples, tallying a number of a plurality of sequencing reads corresponding to a plurality of repeat units with a plurality of different numbers of a plurality of repeating base pairs spanning the MSI locus, and total number ($n_{total}$) of the plurality of sequencing reads corresponding to all of the plurality of repeat units at the MSI locus;

S3-2: sorting the plurality of repeat units with the plurality of different numbers of the plurality of repeating base pairs in descending order according to corresponding numbers to the plurality of sequencing reads, recording the number of the plurality of sequencing reads as n(j), wherein j=1, 2, 3 . . . etc.; individually calculating a percentage [A(j)] of the n(j) to a total number of the plurality of sequencing reads: $A(j)=n(j)/n_{total}*100\%$; and S3-3: sequentially calculating a cumulative percentage B for m=1, 2, 3 . . . etc., using the formula below:

$$B = \sum_{j=1}^{m} A(j);$$

as soon as B≥a threshold percentage, stopping a calculation and defining the plurality of repeat units with the plurality of different numbers of the plurality of repeating base pairs corresponding to A(1) to A(m) as the plurality of principal repeat unit species; wherein the threshold percentage is 90%.

3. The method for analyzing the sequencing data of the microsatellite instability according to claim 1, wherein the plurality of population principal repeat unit species in the step S2-3 is calculated by the following steps:

S4-1: pooling the sequencing data of all of the plurality of normal samples as a whole, and tallying a number of a plurality of sequencing reads corresponding to a plurality of repeat units with a plurality of different numbers of a plurality of repeating base pairs spanning the MSI locus, and a total number ($n_{total}$) of the plurality of sequencing reads corresponding to all of the plurality of repeat units at the MSI locus;

S4-2: sorting the plurality of repeat units with the plurality of different numbers of the plurality of repeating base pairs in descending order according to corresponding numbers to the plurality of sequencing reads, recording the number of the plurality of sequencing reads as n(j), wherein j=1, 2, 3 . . . etc.; individually calculating a percentage [A(j)] of the n(j) to a total number of the plurality of sequencing reads: A(j)=n(j)/$n_{total}$*100%; and S4-3: sequentially calculating a cumulative percentage B for m=1, 2, 3 . . . etc., using the formula below:

$$B = \sum_{j=1}^{m} A(j);$$

as soon as B≥a threshold percentage, stopping a calculation and defining the plurality of repeat units with the plurality of different numbers of the plurality of repeating base pairs corresponding to A(1) to A(m) as the plurality of population principal repeat unit species, wherein the threshold percentage is 90%.

4. The method for analyzing the sequencing data of the microsatellite instability according to claim 1, wherein in the step S2-3, calculating the proportion of the plurality of population principal repeat unit species in the each of the plurality of normal samples is performed by counting a number (n) of a plurality of sequencing reads corresponding to each of the plurality of population principal repeat unit species at the MSI locus in the each of the plurality of normal samples, and then calculating a proportion of the number (n) of the plurality of sequencing reads to a total number ($n_{total}$) of the plurality of sequencing reads spanning the MSI locus in the normal sample.

5. The method for analyzing the sequencing data of the microsatellite instability according to claim 1, wherein the method further comprises step S5: calculating a proportion of a plurality of microsatellite loci determined to be unstable among all tested microsatellite loci, and performing statistical analysis on proportion data of a plurality of samples to qualitatively determine thresholds used to define the plurality of samples as MSS, MSI-L or MSI-H; wherein in the step S1, a target gene DNA is enriched by a liquid phase capture in the NGS sequencing; more preferably, the target gene DNA is enriched using 120 bp biotinylated single-stranded DNA probes by the liquid phase capture in the NGS sequencing; in the step S2, three determination criteria are simultaneously used, and if at least one of the three determination criteria is satisfied, the MSI locus of the sample is considered as unstable; the MSI locus has mononucleotide repeats and comprises a combination of any 16, 17, 18, 19, 20, 21 or 22 of the following 22 gene loci: BAT25, BAT26, NR24, NR21, Mono27, NR22, NR27, BAT40, CUL-22, MET-15, ATM-15, RB1-13, NF1-26, DDR-11, FANC-21, MITF-14, PKHD-18, PTK-16, RET-14, CBL-17, PTPN-17, and SMAD-18.

6. A device for detecting microsatellite instability, comprising
a sequencing data reading module configured to read sample sequencing data obtained and stored from a sequencing device;
a principal repeat unit species determining module configured to analyze the sample sequencing data to obtain a plurality of principal repeat unit species of a microsatellite locus in each of a plurality of normal samples or a plurality of test samples;
a population principal repeat unit species determining module configured to analyze the sample sequencing data to obtain a plurality of population principal repeat unit species in all of the plurality of normal samples;
a determining module configured to determine whether a Microsatellite Instability (MSI) locus is in an unstable status, and include one or more of a first analyzing module, a second analyzing module and a third analyzing module to identify a stable or the unstable status of each MSI locus in each of the plurality of normal samples or the plurality of test samples to provide a genomic locus suitable for use as a microsatellite instability indicator, wherein
the first analyzing module is configured to obtain the plurality of principal repeat unit species at the MSI locus of the each of the plurality of test samples and the plurality of normal samples obtained from the principal repeat unit species determining module, tally a number ($N_i$) of the plurality of principal repeat unit species in the each of the plurality of normal samples, and calculate mean value [mean($N_i$)] of the $N_i$ and standard deviation [sd($N_i$)]; if a number of the plurality of principal repeat unit species at the MSI locus in a test sample is larger than mean($N_i$)+x*sd($N_i$), then the MSI locus in the test sample is determined as an unstable microsatellite locus, wherein x is a coefficient of standard deviation, and x=3;
the second analyzing module is configured to obtain the plurality of principal repeat unit species at the MSI locus of the each of the plurality of test samples and the plurality of normal samples obtained from the principal repeat unit species determining module, and determine whether the plurality of principal repeat unit species that have not appeared in any of the plurality of normal samples are present in the test sample at the MSI locus; if present, then the MSI locus in the test sample is determined as the unstable microsatellite locus;
the third analyzing module is configured to obtain the plurality of population principal repeat unit species of all of the plurality of normal samples obtained from the population principal repeat unit species determining module, and then calculate a proportion of the plurality of population principal repeat unit species in the each of the plurality of normal samples, perform statistical analysis according to the proportion to obtain a distribution reference set and calculate median [Q2($R_i$)], first quartile [Q1($R_i$)] and third quartile [Q3($R_i$)] of the proportion, and calculate a proportion ($RT_i$) of the plurality of population principal repeat unit species in the each of the plurality of test samples; if $RT_i$>Q2($R_i$)+1.5*(Q3($R_i$)−Q1($R_i$)) or $RT_i$<Q2($R_i$)−1.5*(Q3($R_i$)−Q1($R_i$)), then the MSI locus in the test sample is determined as the unstable microsatellite locus.

7. The device for detecting the microsatellite instability according to claim 6, wherein the determining module comprises the first analyzing module, the second analyzing module and the third analyzing module, and the determining module is configured to obtain a plurality of analysis results from the first analyzing module, the second analyzing module and the third analyzing module, and if the plurality of analysis results from any one of the first analyzing module, the second analyzing module and the third analyzing module show a microsatellite instability status, then the determining module determines that the test sample is in the microsatellite instability status.

8. The device for detecting the microsatellite instability according to claim 6, wherein the principal repeat unit species determining module is configured to tally a number of a plurality of sequencing reads corresponding to a plurality of repeat units with a plurality of different numbers of a plurality of repeating base pairs spanning the MSI locus, and a total number ($n_{total}$) of the plurality of sequencing reads corresponding to all of the plurality of repeat units at the MSI locus, according to a sequencing result of one of a plurality of samples; sort the plurality of repeat units with the plurality of different numbers of the plurality of repeating base pairs in descending order according to corresponding numbers to the plurality of sequencing reads, the number of the plurality of sequencing reads being recorded as n(j), wherein j=1, 2, 3 . . . etc.; individually calculate a percentage [A(j)] of the n(j) to the total number of the plurality of sequencing reads: A(j)=n(j)/$n_{total}$*100%; and sequentially calculate a cumulative percentage B for m=1, 2, 3 . . . etc., using the formula below:

$$B = \sum_{j=1}^{m} A(j);$$

wherein when B≥a threshold percentage, a calculation is stopped and the plurality of repeat units with the plurality of different numbers of the plurality of repeating base pairs corresponding to A(1) to A(m) are determined as the plurality of principal repeat unit species; and the threshold percentage is 90%.

9. The device for detecting the microsatellite instability according to claim 6, wherein the population principal repeat unit species determining module is configured to pool the sequencing data of all of the plurality of normal samples as a whole, tally a number of a plurality of sequencing reads corresponding to a plurality of repeat units with a plurality of different numbers of a plurality of repeating base pairs spanning the MSI locus, and a total number ($n_{total}$) of the plurality of sequencing reads corresponding to all of the plurality of repeat units at the MSI locus; sort the plurality of repeat units with the plurality of different numbers of the plurality of repeating base pairs in descending order according to corresponding numbers to the plurality of sequencing reads, the number of the plurality of sequencing reads being recorded as n(j), wherein j=1, 2, 3 . . . etc.; individually calculate a percentage [A(j)] of the n(j) to the total number of the plurality of sequencing reads: A(j)=n(j)/$n_{total}$*100%; and sequentially calculate a cumulative percentage B for m=1, 2, 3 . . . etc., using the formula below:

$$B = \sum_{j=1}^{m} A(j);$$

wherein when B≥a threshold percentage, a calculation is stopped and the plurality of repeat units with the plurality of different numbers of the plurality of repeating base pairs corresponding to A(1) to A(m) are determined as the plurality of population principal repeat unit species; and the threshold percentage is 90%.

10. A non-transitory computer readable medium, wherein the non-transitory computer readable medium records programs for performing the method for analyzing the sequencing data of the microsatellite instability according to claim 1.

11. The non-transitory computer readable medium, wherein the non-transitory computer readable medium records programs for performing the method for analyzing the sequencing data of the microsatellite instability according to claim 10, wherein the plurality of principal repeat unit species in the step S2-1 and the step S2-2 is calculated by the following steps:

S3-1: according to a sequencing result of one of a plurality of samples, tallying a number of a plurality of sequencing reads corresponding to a plurality of repeat units with a plurality of different numbers of a plurality of repeating base pairs spanning the MSI locus, and total number ($n_{total}$) of the plurality of sequencing reads corresponding to all of the plurality of repeat units at the MSI locus;

S3-2: sorting the plurality of repeat units with the plurality of different numbers of the plurality of repeating base pairs in descending order according to corresponding numbers to the plurality of sequencing reads, recording the number of the plurality of sequencing reads as n(j), wherein j=1, 2, 3 . . . etc.; individually calculating a percentage [A(j)] of the n(j) to a total number of the plurality of sequencing reads: A(j)=n(j)/$n_{total}$*100%; and S3-3: sequentially calculating a cumulative percentage B for m=1, 2, 3 . . . etc., using the formula below:

$$B = \sum_{j=1}^{m} A(j);$$

as soon as B≥a threshold percentage, stopping a calculation and defining the plurality of repeat units with the plurality of different numbers of the plurality of repeating base pairs corresponding to A(1) to A(m) as the plurality of principal repeat unit species; wherein the threshold percentage is 90%.

12. The non-transitory computer readable medium, wherein the non-transitory computer readable medium records programs for performing the method for analyzing the sequencing data of the microsatellite instability according to claim 10, wherein the plurality of population principal repeat unit species in the step S2-3 is calculated by the following steps:

S4-1: pooling the sequencing data of all of the plurality of normal samples as a whole, and tallying a number of a plurality of sequencing reads corresponding to a plurality of repeat units with a plurality of different numbers of a plurality of repeating base pairs spanning the MSI locus, and a total number ($n_{total}$) of the plurality of sequencing reads corresponding to all of the plurality of repeat units at the MSI locus;

S4-2: sorting the plurality of repeat units with the plurality of different numbers of the plurality of repeating base pairs in descending order according to corresponding numbers to the plurality of sequencing reads, recording the number of the plurality of sequencing reads as n(j), wherein j=1, 2, 3 . . . etc.; individually calculating a percentage [A(j)] of the n(j) to a total number of the plurality of sequencing reads: $A(j)=n(j)/n_{total}*100\%$; and S4-3: sequentially calculating a cumulative percentage B for m=1, 2, 3 . . . etc., using the formula below:

$$B = \sum_{j=1}^{m} A(j);$$

as soon as B≥a threshold percentage, stopping a calculation and defining the plurality of repeat units with the plurality of different numbers of the plurality of repeating base pairs corresponding to A(1) to A(m) as the plurality of population principal repeat unit species, wherein the threshold percentage is 90%.

13. The non-transitory computer readable medium, wherein the non-transitory computer readable medium records programs for performing the method for analyzing the sequencing data of the microsatellite instability according to claim 10, wherein in the step S2-3, calculating the proportion of the plurality of population principal repeat unit species in the each of the plurality of normal samples is performed by counting a number (n) of a plurality of sequencing reads corresponding to each of the plurality of population principal repeat unit species at the MSI locus in the each of the plurality of normal samples, and then calculating a proportion of the number (n) of the plurality of sequencing reads to a total number ($n_{total}$) of the plurality of sequencing reads spanning the MSI locus in the normal sample.

14. The non-transitory computer readable medium, wherein the non-transitory computer readable medium records programs for performing the method for analyzing the sequencing data of the microsatellite instability according to claim 10, wherein the method further comprises step S5: calculating a proportion of a plurality of microsatellite loci determined to be unstable among all tested microsatellite loci, and performing statistical analysis on proportion data of a plurality of samples to qualitatively determine thresholds used to define the plurality of samples as MSS, MSI-L or MSI-H; wherein in the step S1, a target gene DNA is enriched by a liquid phase capture in the NGS sequencing; more preferably, the target gene DNA is enriched using 120 bp biotinylated single-stranded DNA probes by the liquid phase capture in the NGS sequencing; in the step S2, three determination criteria are simultaneously used, and if at least one of the three determination criteria is satisfied, the MSI locus of the sample is considered as unstable; the MSI locus has mononucleotide repeats and comprises a combination of any 16, 17, 18, 19, 20, 21 or 22 of the following 22 gene loci: BAT25, BAT26, NR24, NR21, Mono27, NR22, NR27, BAT40, CUL-22, MET-15, ATM-15, RB1-13, NF1-26, DDR-11, FANC-21, MITF-14, PKHD-18, PTK-16, RET-14, CBL-17, PTPN-17, and SMAD-18.

15. The non-transitory computer readable medium, wherein the non-transitory computer readable medium records programs for performing the method for analyzing the sequencing data of the microsatellite instability according to claim 10, comprising a sequencing data reading module configured to read sample sequencing data obtained and stored from a sequencing device;

a principal repeat unit species determining module configured to analyze the sample sequencing data to obtain a plurality of principal repeat unit species of a microsatellite locus in each of a plurality of normal samples or a plurality of test samples;

a population principal repeat unit species determining module configured to analyze the sample sequencing data to obtain a plurality of population principal repeat unit species in all of the plurality of normal samples;

a determining module configured to determine whether a Microsatellite Instability (MSI) locus is in an unstable status, and include one or more of a first analyzing module, a second analyzing module and a third analyzing module, wherein the first analyzing module is configured to obtain the plurality of principal repeat unit species at the MSI locus of the each of the plurality of test samples and the plurality of normal samples obtained from the principal repeat unit species determining module, tally a number ($N_i$) of the plurality of principal repeat unit species in the each of the plurality of normal samples, and calculate mean value [mean($N_i$)] of the $N_i$ and standard deviation [sd($N_i$)]; if a number of the plurality of principal repeat unit species at the MSI locus in a test sample is larger than mean($N_i$)+x*sd($N_i$), then the MSI locus in the test sample is determined as an unstable microsatellite locus, wherein x is a coefficient of standard deviation, and x=3;

the second analyzing module is configured to obtain the plurality of principal repeat unit species at the MSI locus of the each of the plurality of test samples and the plurality of normal samples obtained from the principal repeat unit species determining module, and determine whether the plurality of principal repeat unit species that have not appeared in any of the plurality of normal samples are present in the test sample at the MSI locus; if present, then the MSI locus in the test sample is determined as the unstable microsatellite locus;

the third analyzing module is configured to obtain the plurality of population principal repeat unit species of all of the plurality of normal samples obtained from the population principal repeat unit species determining module, and then calculate a proportion of the plurality of population principal repeat unit species in the each of the plurality of normal samples, perform statistical analysis according to the proportion to obtain a distribution reference set and calculate median [Q2($R_i$)], first quartile [Q1($R_i$)] and third quartile [Q3($R_i$)] of the proportion, and calculate a proportion ($RT_i$) of the plurality of population principal repeat unit species in the each of the plurality of test samples; if $RT_i$>Q2($R_i$)+1.5*(Q3($R_i$)−Q1($R_i$)) or $RT_i$<Q2($R_i$)−1.5*(Q3($R_i$)−Q1($R_i$)), then the MSI locus in the test sample is determined as the unstable microsatellite locus.

16. The non-transitory computer readable medium, wherein the non-transitory computer readable medium records programs for performing the method for analyzing the sequencing data of the microsatellite instability according to claim 10, wherein the determining module comprises the first analyzing module, the second analyzing module and the third analyzing module, and the determining module is configured to obtain a plurality of analysis results from the first analyzing module, the second analyzing module and the third analyzing module, and if the plurality of analysis results from any one of the first analyzing module, the second analyzing module and the third analyzing module show a microsatellite instability status, then the determining module determines that the test sample is in the microsatellite instability status.

17. The non-transitory computer readable medium, wherein the non-transitory computer readable medium records programs for performing the method for analyzing the sequencing data of the microsatellite instability according to claim 10, wherein the principal repeat unit species determining module is configured to tally a number of a plurality of sequencing reads corresponding to a plurality of repeat units with a plurality of different numbers of a plurality of repeating base pairs spanning the MSI locus, and a total number ($n_{total}$) of the plurality of sequencing reads corresponding to all of the plurality of repeat units at the MSI locus, according to a sequencing result of one of a plurality of samples; sort the plurality of repeat units with the plurality of different numbers of the plurality of repeating base pairs in descending order according to corresponding numbers to the plurality of sequencing reads, the number of the plurality of sequencing reads being recorded as n(j), wherein j=1, 2, 3 . . . etc.; individually calculate a percentage [A(j)] of the n(j) to the total number of the plurality of sequencing reads: $A(j)=n)/n_{total}*100\%$; and sequentially calculate a cumulative percentage B for m=1, 2, 3 . . . etc., using the formula below:

$$B = \sum_{j=1}^{m} A(j);$$

wherein when B≥a threshold percentage, a calculation is stopped and the plurality of repeat units with the plurality of different numbers of the plurality of repeating base pairs corresponding to A(1) to A(m) are determined as the plurality of principal repeat unit species; and the threshold percentage is 90%.

18. The non-transitory computer readable medium, wherein the non-transitory computer readable medium records programs for performing the method for analyzing the sequencing data of the microsatellite instability according to claim 10, wherein the population principal repeat unit species determining module is configured to pool the sequencing data of all of the plurality of normal samples as a whole, tally a number of a plurality of sequencing reads corresponding to a plurality of repeat units with a plurality of different numbers of a plurality of repeating base pairs spanning the MSI locus, and a total number ($n_{total}$) of the plurality of sequencing reads corresponding to all of the plurality of repeat units at the MSI locus; sort the plurality of repeat units with the plurality of different numbers of the plurality of repeating base pairs in descending order according to corresponding numbers to the plurality of sequencing reads, the number of the plurality of sequencing reads being recorded as n(j), wherein j=1, 2, 3 . . . etc.; individually calculate a percentage [A(j)] of the n(j) to the total number of the plurality of sequencing reads: $A(j)=n(j)/n_{total}*100\%$; and sequentially calculate a cumulative percentage B for m=1, 2, 3 . . . etc., using the formula below:

$$B = \sum_{j=1}^{m} A(j);$$

wherein when B≥a threshold percentage, a calculation is stopped and the plurality of repeat units with the plurality of different numbers of the plurality of repeating base pairs corresponding to A(1) to A(m) are determined as the plurality of population principal repeat unit species; and the threshold percentage is 90%.

* * * * *